(12) United States Patent
Schmitt et al.

(10) Patent No.: US 9,816,149 B2
(45) Date of Patent: *Nov. 14, 2017

(54) DIAGNOSTIC TRANSCRIPT AND SPLICE PATTERNS OF HR-HPV IN DIFFERENT CERVICAL LESIONS

(75) Inventors: Markus Schmitt, Heidelberg (DE); Lutz Gissmann, Wiesloch (DE); Michael Pawlita, Eschelbronn (DE); Daniela Hoefler, Heidelberg (DE)

(73) Assignee: Deutsches Krebsforschungzentrum (DE)

( * ) Notice: Subject to any disclaimer, the term of this patent is extended or adjusted under 35 U.S.C. 154(b) by 484 days.

This patent is subject to a terminal disclaimer.

(21) Appl. No.: 13/101,020

(22) Filed: May 4, 2011

(65) Prior Publication Data
US 2011/0275059 A1 Nov. 10, 2011

Related U.S. Application Data

(60) Provisional application No. 61/331,561, filed on May 5, 2010.

(51) Int. Cl.
*C12Q 1/68* (2006.01)
*C12P 19/34* (2006.01)
*C12Q 1/70* (2006.01)

(52) U.S. Cl.
CPC .......... *C12Q 1/708* (2013.01); *C12Q 1/6883* (2013.01)

(58) Field of Classification Search
None
See application file for complete search history.

(56) References Cited

U.S. PATENT DOCUMENTS

| 5,876,937 A | 3/1999 | Sillekens | |
|---|---|---|---|
| 2012/0040334 A1* | 2/2012 | Schmitt et al. ................ | 435/5 |

FOREIGN PATENT DOCUMENTS

| JP | 2002537779 A | 11/2002 |
|---|---|---|
| JP | 2005501650 A | 1/2005 |
| WO | PCTEP2009064811 | 2/2010 |
| WO | PCTEP2009064811 | 4/2011 |

OTHER PUBLICATIONS de Boer (Clin Cancer Res 2007, 13:132-138).*
Kraus (Cancer Res 2008, 68: 2514-2522).*
Klaes et al. (Cancer Research, 1999, 15, 6132-63136).*
Soeda et al. (Virology 2006;351: 29-41.*
Höfler D. HPV16 RNA patterns as diagnostic marker for cervical cancer precursor lesions: Validation by newly developed high-throughput RT-qPCR [dissertation]. Heidelberg (Germany): Ruperto-Carola University, 2013).*

Alloul, Nathalie, et al., 1999, "Transcription-modulatory activities of differentially spliced cDNAs encoding the E2 protein of human papillomavirus type 16", Journal of General Virology, 80:2461-2470.
Greijer, Astrid E., et al., 2000, "Human Cytomegalovirus Virions Differentially Incorporate Viral and Host Cell RNA during the Assembly Process", Journal of Virology, 74(19):9078-9082.
Hoyer, Heike, et al., 2005, "Cumulative 5-year diagnoses of CIN2, CIN3 or cervical cancer after concurrent high-risk HPV and cytology testing in a primary screening setting", International Journal of Cancer, 116:136-143.
Kraus, I, et al., 2004, "Human papillomavirus oncogenic expression in the dysplasic portio; an investigation of biopsies from 190 cervical cones", British Journal of Cancer, 90:1407-1413.
Molden, Tor, et al., 2007, "PreTect HPV-Proofer: Real-time detection and typing of E6/E7 mRNA from carcinogenic human papillomaviruses", Journal of Virological Methods, 142:204-212.
Pim, David, et al., 1997, "Alternatively spliced HPV-18 E6* protein inhibits E6 mediated degradation of p53 and suppresses transformed cell growth", Oncogene, 15:257-264.
Sherman, L., et al., 1992, "Human Papillomavirus Type 16 Expresses a Variety of Alternatively Spliced mRNSs Putatively Encoding the E2 Protein", Virology, 191:953-959.
Soltar, Karl, et al., 2004, "Detection of High-Risk Human Papillomavirus E6 and E7 Oncogene Transcripts in Cervical Scrapes by Nested RT-Polymerase Chain Reaction", Journal of Medical Virology, 74:107-116.
Wang-Johanning, Feng, et al., 2002, "Quantitation of Human Papillomavirus 16 E6 and E7 DNA and RNA in Residual Material from ThinPrep Papanicolaou Tests Using Real-Time Polymerase Chain Reaction Analysis", Cancer, 94:2199-2210.
Zerbini, M., et al., 2006, "Analysis of HPV16 E6*I-II transcripts in cervical samples", Journal of Clinical Virology, 36 (S2):S8.
Zheng, Zhi-Ming, et al., 2006, "Papillomavirus genome structure, expression, and post-transcriptional regulations", Frontiers in Bioscience, 11:2286-2302.
Baker, Carl, et al., 1996, "Maps of Papillomavirus mRNA Transcripts", Los Alamos National Laboratories, Los Alamos, NM, USA.
Baldwin, Peter, et al., 2003, "Translational approaches to improving cervical screening", Nature Reviews, 3:217-226.
Birner, Peter, et al., 2001, "Signal-Amplified Colorimetric In Situ Hybridization for Assessment of Human Papillomavirus Infection in Cervical Lesions", Modern Pathology 14(7):702-709.
Bulkmans, N. W. J., et al, 2007, "Human papillomavirus DNA testing for the detection of cervical intraepithelial neoplasia grade 3 and cancer: 5-year follow-up of a randomized controlled implementation trial", Lancet, 370:1764-1772.
Castle, Philip, et al. 2008, "Human Papillomaviurs Genotype Specificity of Hybrid Capture 2", Journal of Clinical Microbiology, 46(8):2595-2604.

(Continued)

*Primary Examiner* — Sarae Bausch
(74) *Attorney, Agent, or Firm* — J.A. Lindeman & Co., PLLC

(57) ABSTRACT

The present invention relates to a method for differentiating in a subject with HR-HPV between a severe form of HR-HPV infection and a mild form of HR-HPV infection. It further is concerned with a composition comprising a probe oligonucleotide mixture, a device, and a kit for use in conjunction with the method of the invention.

11 Claims, No Drawings

(56) References Cited

OTHER PUBLICATIONS

Cuschieri, Kate S., et al., 2004, "Human Papillomavirus Type Specific DNA and RNA Persistence—Implications for Cervical Disease Progression and Monitoring", Journal of Medical Virology, 73:65-70.
De Villiers, Ethel-Michele, 2004, "Classification of papillomaviruses", Virology, 324:17-27.
Dallenbach-Hellweg, Gisela, et al. 2004, "Traditional and New Molecular Methods for Early Detection of Cervical Cancer", Ark. Pathology, 66(5):35-39.
Gheit, Tarik, et al., 2009, "Prevalence of human papillomavirus types in cervical and oral cancers in central India", Vaccine, 27:636-639.
Molijn, Anco, et al. 2005, "Molecular diagnosis of human papillomavirus (HPV) infections", Journal of Clinical Virology, 32S:S43-S51.
Myers, G., et al. 1997, "Human Papillomaviruses 1997: a compilation and analysis of nucleic acid and amino acid sequences", Theoretical Biology and Biophysics, Los Alamos National Laboratory, Los Alamos, New Mexico.
Pett, M. et al.., 2007, "Integration of high-risk human papillomavirus: a key event in cervical carcinogenisis?", Journal of Pathology, 212:356-367.
Sabol, Ivan, et al., 2008, "Evaluation of Different Techniques for Identification of Human Papillomavirus Types of Low Prevalence", Journal of Clinical Microbiology, 46(5): 1606-1613.
Schmitt, Markus, et al., 2006, "Bead-Based Multiplex Genotyping of Human Papillomaviruses", Journal of Clinical Microbiology, 44(2): 504-512.
Schmitt, Markus, et al., 2010, "Diagnosing Cervical Cancer and High-Grade Precursors by HPV16 Transcription Patterns", 70:249-256.
Schmitt, Markus, et al., 2010, "Abundance of Multiple High-Risk Human Papillomavirus (HPV) Infections Found in Cervical Cells Analyzed by Use of an Ultrasensitive HPV Genotyping Assay", Journal of Clinical Microbiology, 48(1):143-149.
Smith, J. H. F. 2002, "Bethesda 2001", Cytopathology, 13:4-10.
Van Gemen, Bob, et al, 1993, "Quantification of HIV-1 RNA in plasma using NASBA during HIV-1 primary infection", Journal of Virological Methods, 43:177-188.
Vinokurova, Svetlana, et al., 2008, "Type-Dependent Integration Frequency of Human Papillomavirus Genomes in Cervical Lesions", 68:307-313.
Zheng, Zhi-Ming, 2006, "Papillomavirus Genome Structure, Expression, and Post-Transcriptional Regulation", Front Biosci., 2286-2302.
Hoyer, H., C. Scheungraber, R. Kuehne-Heid, K. Teller, C. Greinke, S. Leistritz, B. Ludwig, M. Durst, and A. Schneider. 2005. Cumulative 5-year diagnoses of CIN2, CIN3 or cervical cancer after concurrent high-risk HPV and cytology testing in a primary screening setting. Int. J. Cancer 116:136-143.
Compton, J. 1991. Nucleic acid sequence-based amplification. Nature 350:91-92.
Sotlar K, Stubner A, Diemer D, et al. Detection of high-risk human papillomavirus E6 and E7 oncogene transcripts in cervical scrapes by nested RT-polymerase chain reaction. Journal of medical virology 2004;74:107-116.
Pim D, Massimi P, Banks L. Alternatively spliced HPV-18 E6* protein inhibits E6 mediated degradation of p53 and suppresses transformed cell growth. Oncogene 1997;15:257-264.
Meyers C, Mayer TJ, Ozbun MA. Synthesis of infectious human papillomavirus type 18 in differentiating epithelium transfected with viral DNA. J. Virol. 1997;71:7381-7386.
Snijders PJ, van den Brule AJ, Schrijnemakers HF, Raaphorst PM, Meijer CJ, Walboomers JM. Human papillomavirus type 33 in a tonsillar carcinoma generates its putative E7 mRNA via two E6* transcript species which are terminated at different early region poly(A) sites. J. Virol. 1992;66:3172-3178.
Alloul, N., and L. Sherman. 1999. Transcription-modulatory activities of differentially spliced cDNAs encoding the E2 protein of human papillomavirus type 16. J. Gen. Virol. 80 (Pt 9):2461-2470.
Köhler and Milstein, Nature 256 (1975), 495, and Galfré, Meth. Enzymol. 73 (1981).
Malmborg, J. Immunol. Methods 183 (1995), 7-13.

* cited by examiner

DIAGNOSTIC TRANSCRIPT AND SPLICE PATTERNS OF HR-HPV IN DIFFERENT CERVICAL LESIONS

CROSS REFERENCE TO RELATED APPLICATIONS

This application claims benefit of priority to provisional patent application Ser. No. 61/331,561, filed May 5, 2010, the contents of which is incorporated by reference herein in its entirety.

REFERENCE TO SEQUENCE LISTING

This application contains a Sequence Listing submitted as an electronic text file named "26785-US Sequence listing.txt", having a size in bytes of 77 kb, and created on Apr. 29, 2011. The information contained in this electronic file is hereby incorporated by reference in its entirety pursuant to 37 CFR §1.52(e)(5).

FIELD OF INVENTION

The present invention relates to a method for differentiating in a subject with high-risk (HR)-HPV between a severe form of HR-HPV infection and a mild form of HR-HPV infection. It further is concerned with a composition comprising a probe oligonucleotide mixture, a device, and a kit for use in conjunction with the method of the invention.

BACKGROUND OF THE INVENTION

Cancer of the uterine cervix (CxCa) is the second most common malignancy in women worldwide and is caused by high-risk human papillomaviruses with HPV16 being the most prevalent type. In developed countries, conventional cytological screening programs have substantially reduced the incidence of this kind of cancer. These cytological screening programs, however, have some drawbacks.

The Papanicolaou test, frequently also referred to as Pap test, is a diagnostic method designed for the detection of premalignant and malignant lesion in the uterine cervix. For the Papanicolaou test, samples are obtained from the cervix and screened by light microscopy for changes in cell morphology indicating malignant or premalignant cells. Then, samples are classified depending on the severity of the observed lesions. However, diagnosis by cervical cytology is a subjective method, and the quality depends on the standards of the laboratory that provides the service. As such, lesion categorization is only moderately reproducible and of poor sensitivity compared to colposcopy (Baldwin, P., R. Laskey, and N. Coleman. 2003. Translational approaches to improving cervical screening. Nat Rev Cancer 3:217-26). Moreover, false positive results lead to a high number of patients that are being over-treated.

Within the last two decades a variety of new diagnostic tests for HPV were developed. These methods are based on the detection of viral, molecular and biochemical markers, such as HPV proteins, DNA and RNA.

The FDA-approved Hybrid Capture II Test System (HC2) (formerly Digene Corp., USA, now Qiagen, the Netherlands) is considered the gold standard for HPV DNA testing in clinical practice, however, it shows several disadvantages: a) no genotyping is performed, instead HPV infection is solely attributed to a "low-risk" or "high-risk" group, b) multiple infections cannot be identified, c) it is less sensitive for HPV detection than PCR-based methods (Birner et al. 2001. Mod. Pathol. 14:702-709), and d) it is modestly specific for predicting of cervical precancer and cancer risk. Some of its non-specificity for clinical end points can be ascribed to cross-reactivity with non-carcinogenic HPV genotypes (Castle, P. E., D. Solomon, C. M. Wheeler, P. E. Gravitt, S. Wacholder, and M. Schiffman. 2008. Human papillomavirus genotype specificity of hybrid capture 2.3 Clin Microbiol 46:2595-604). Moreover, it only allows for the assessment whether a subject is infected with HPV or not. The test does not allow for assessing the severity of a HPV infection. Thus, once HPV has been diagnosed, further examinations are required.

Several PCR-based methods were developed within the last years, allowing a more precise detection of HPV infection. The majority of these PCR systems use consensus or general primers that bind to highly conserved regions of the HPV genome, e.g. in the L1 region. The amplified PCR products are then subjected to further analysis (e.g. sequencing, restriction fragment length polymorphism (RFLP) analysis or hybridization) in order to identify specific mucosal HPV genotypes. Longitudinal cohort studies have shown that combined Pap and HPV testing exhibit better sensitivity and predict better long-term protection (among women with normal results of both tests) against CIN3 than cytological testing alone (Bulkmans, N. W., J. Berkhof, L. Rozendaal, F. J. van Kemenade, A. J. Boeke, S. Bulk, F. J. Voorhorst, R. H. Verheijen, K. van Groningen, M. E. Boon, W. Ruiting a, M. van Ballegooijen, P. J. Snijders, and C. J. Meijer. 2007. Human papillomavirus DNA testing for the detection of cervical intraepithelial neoplasia grade 3 and cancer: 5-year follow-up of a randomised controlled implementation trial. Lancet 370:1764-72, Hoyer, H., C. Scheungraber, R. Kuehne-Heid, K. Teller, C. Greinke, S. Leistritz, B. Ludwig, M. Durst, and A. Schneider. 2005. Cumulative 5-year diagnoses of CIN2, CIN3 or cervical cancer after concurrent high-risk HPV and cytology testing in a primary screening setting. Int J Cancer 116:136-43.). However, the high sensitivity of HPV PCR tests leads also to the identification of clinically not relevant infections or regressing lesions. Therefore, the positive predictive value (PPV) for the presence of an advanced lesion or the development of cervical cancer after an individual high-risk HPV DNA positive result is low. The resulting high proportion of test-positive but disease-negative diagnoses cause over-treatment, additional costs and considerable anxiety for women concerned (International Agency for Research on Cancer. 2005. Cervix Cancer Screening. IARC Press, Lyon).

Unlike HPV DNA testing, RNA detection allows the identification and analysis of transcriptionally active viruses. A recent introduction of preservation media for cervical smears that, apart from DNA and cell morphology, also conserves RNA, enhanced the development of RNA detection methods. To date, two commercial HPV RNA detection assays have been introduced: i) PreTect HPV Proofer® from Biomérieux (formerly NorChip) that detects early full-length mRNA targeting E6 and E7 sequences (E6/E7) from HR-HPV types 16, 18, 31, 33 and 45, and ii) the Aptima® HPV test, a broad spectrum E6/E7 full-length mRNA amplification method from GenProbe. Limited data from these tests indicate that testing for full-length HPV E6/E7 mRNA rather than HPV DNA alone only slightly increases the PPV for the development of cervical cancer and its precursors, while at the same time, sensitivity and thus the negative predictive value (NPV) is reduced (Cuschieri, K. S., M. J. Whitley, and H. A. Cubie. 2004. Human papillomavirus type specific DNA and RNA persistence—implications for cervical disease progression and monitoring. J Med Virol 73:65-70). The main disadvantage of these technologies refers to the fact that they cannot predict disease due to only qualitative measurement of a single full-length viral oncogene transcript. Moreover, cervical smears can comprise different amounts of HPV-infected cells that cannot be controlled for by these technologies.

The development of cervical cancer is closely linked to the integration of the HPV genome into the chromosome of the host cells. In low-grade lesions, the majority of HPV genomes are present in an episomal state, whereas in high-grade lesions and carcinoma, the HPV genome can be integrated into the host genome. However, it has been demonstrated that not in all cases of cervical carcinoma the HPV genome is present in an integrated form (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13.). Integration of the HPV16 genome into the host genome is only found in app. 60% of cervical cancer cases. Thus, diagnostic means which determine only the integration status of the HPV genome are not reliable for risk stratification.

It has been proposed that quantification of certain transcripts of HPV16, e.g. the E1C transcript, and comparing the amounts of these transcripts to the amount of a reference transcript is of great value (Schmitt et al. (2010), "Diagnosing Cervical Cancer and High-Grade Precursors by HPV16 Transcription Patterns", Cancer Res. 70: 249-256) in the prediction of disease progression. This, however, could only be shown for HPV16 so far.

Colposcopy allows for examining the uterine cervix and vagina. By this visual examination, many premalignant lesions and malignant lesions in these areas can be detected. Due to its high reliability, colposcopy is regarded to be the goldstandard for diagnosing cervical diseases. This diagnostic procedure, however, is cost- and time-intensive. Colposcopy requires highly trained personnel and often involves an invasive procedure (biopsy with subsequent histologic analysis). Consequently, colposcopy cannot be used in cervical cancer precursor screening programs.

The technical problem underlying the present invention may be seen as the provision of means and methods for efficiently and reliably differentiating between mild and severe forms of infection with high-risk HPV genotypes (HR-HPV) without the drawbacks as referred to above. Also, means and methods are required for a reliable risk stratification of subjects not having the HPV genome integrated into the genome. The technical problem is solved by the embodiments characterized in the claims and herein below.

BRIEF SUMMARY OF THE INVENTION

Accordingly, the current invention relates to a method for differentiating in a subject with HR-HPV between (i) a severe form of HR-HPV infection and (ii) a mild form of HR-HPV infection, said subject not comprising the HR-HPV genome in an integrated form, comprising the steps a) determining, in a sample of said subject, the presence or absence of a gene product of E1C, and b) differentiating between (i) a severe form of HR-HPV infection and (ii) a mild form of HR-HPV infection.

The method of the present invention, preferably, is an in vitro method. Moreover, it may comprise steps in addition to those explicitly mentioned above. For example, further steps may relate to sample pre-treatments or evaluation of the results obtained by the method. The method of the present invention preferably is used for differentiating between mild and severe form of HR-HPV infection in subjects being infected with HR-HPV. However, the method of the present invention may also be used for monitoring, confirmation, and sub-classification of said subject. The method may be carried out manually or assisted by automation. Preferably, steps (a) and/or (b) may in total or in part be assisted by automation, e.g., by a suitable robotic and sensory equipment for the determination in step (a), or a computer-implemented calculation or comparison step in step (b).

DETAILED DESCRIPTION OF THE INVENTION

The term "differentiating" as used herein means to distinguish between (i) a mild form of HR-HPV infection and (ii) a severe form of HR-HPV infection. The term as used herein, preferably, includes differentially diagnosing/detecting a mild and severe form of HR-HPV infection.

As will be understood by those skilled in the art, the aforementioned differentiation is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.001. Preferably, the probability envisaged by the present invention allows that the differentiation will be correct for at least 60%, at least 70%, at least 80%, or at least 90% of the subjects of a given cohort.

The term "subject" as used herein relates to animals, preferably mammals, and, more preferably, humans. However, it is envisaged in accordance with the aforementioned method of the present invention that the subject shall be infected with HR-HPV. Preferably, the subject is infected with HR-HPV selected from the group consisting of HPV18, HPV33, HPV35, HPV52, or HPV58 (see elsewhere herein). How to assess whether a subject is infected with HR-HPV is well known in the art. E.g., HR-HPV infection can be assessed by genotyping HR-HPV DNA in a sample of a subject by Southern and dot blot hybridisation, in situ hybridisation, by signal amplification assays, or by various PCR methods (Molijn, A., B. Kleter, W. Quint, and L. J. van Doorn. 2005. Molecular diagnosis of human papillomavirus (HPV) infections. J Clin Virol 32 Suppl 1:S43-51).

The term "not comprising the HR-HPV genome in an integrated form" as used herein relates to absence of HR-HPV DNA covalently linked to the chromosomal DNA of the host cell. The terms "integrated" and "episomal" are understood by the skilled person. It is to be understood that, if the HR-HPV genome is integrated into the genome of a subject, not the entire cells of said subject will have the HR-HPV genome integrated into its genome. Preferably, only cells that are affected by HR-HPV infection may comprise the HR-HPV genome in an integrated form. Preferably, said cells are present in the urogenital or oropharyngeal tract of said subject. It is to be understood that the term "integrated form" also encompasses the integration of parts of the HR-HPV into chromosomal DNA of the host cell.

Preferably, the early region of the HR-HPV genome, including genes for E6, E7 and parts of the E1 N-terminus, is integrated into the host genome. It is to be understood that also the late region, including the E4, E5 and L1 genes, of the HR-HPV genome may be integrated into the host genome, however, most preferably, are transcriptionally inactive due to genomic rearrangements. Moreover, it is known that the E2 gene is usually lost during integration or transcriptionally inactivated (Pett, M., and N. Coleman. 2007. Integration of high-risk human papillomavirus: a key event in cervical carcinogenesis? J Pathol 212:356-67). The HR-HPV genome is, preferably, present in an "episomal form" in a host cell, if said genome replicates in said host cell without being integrated into the chromosomal DNA of the host cell (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13).

High-risk HPV types, apart from HPV 16 are well known contributing to ~45% of all cervical cancers. It has been demonstrated that integration plays an important role in the carcinogenesis of all high-risk HPV types. However, for high-risk HPV types 16 and phylogenetically related types 31 and 33, integration occurs less frequently, suggesting a second mode of progression such as a potential E1C-mediated upregulation of the LCR or, as the E1C and E2 open reading frames overlap, by a suppression of E2 translation after translation termination of E1C. But still for a large proportion cervical cancer caused by these HPV types and for a very high proportion of cervical cancers caused by other types, including HPV 18, and 45, integration is the key event in the development of cervical cancer (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13).

How to assess the integration status of the HR-HPV genome is well known in the art. Preferably, the integration status is determined in a sample of the subject. Preferred methods for determining the integration status are (i) methods that detect virus-host fusion transcripts, particularly transcriptionally active viral integrants, e.g. by amplification of papillomavirus oncogene transcripts (APOT-assay) and RNA in situ hybridisation (ISH); and (ii) methods that detect integrated viral DNA regardless of its transcriptional status, e.g. Southern blotting, quantitative real-time PCR, restriction-site PCR, and DNA ISH (Pett, M., and N. Coleman. 2007. Integration of high-risk human papillomavirus: a key event in cervical carcinogenesis? J Pathol 212:356-67).

Generally, subjects comprising the HR-HPV genome in an episomal form only are considered to be at a lower risk for suffering from HSIL or cancer than subjects with the HPV16 genome in an integrated form (for an explanation of the terms "episomal form" and "integrated forms" see herein above). However, there is evidence that some subjects comprising the HPV genome only in an episomal form suffer from severe forms of HPV infection or are at elevated risk of suffering thereof (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13, Pett, M., and N. Coleman. 2007. Integration of high-risk human papillomavirus: a key event in cervical carcinogenesis? J Pathol 212:356-67).

The term "human papillomavirus" (HPV) relates to a DNA virus from the papillomaviridae family of viruses that infects the skin and mucous membranes of humans. More than 110 HPV genotypes have been described (de Villiers, E. M., C. Fauquet, T. R. Broker, H. U. Bernard, and H. zur Hausen. 2004. Classification of papillomaviruses. Virology 324:17-27). Approximately 50 HPV genotypes are known to infect the mucosa. These mucosal genotypes are classified into three different groups based on their epidemiological association with cancer: "low-risk" human papillomaviruses (LR-HPV), "high-risk" human papillomaviruses (HR-HPV) and "putative high-risk" human papillomaviruses (pHR-HPV). Preferably, HPVs are High-risk HPV genotypes (HR-HPVs), which are the main cause for the development of cervical cancer, more preferably HPVs are HPV 31, 39, 45, 51, 52, 56, 58, 59, 68, 73 and 82, most preferably HPV 18 (Genbank Acc. No: NC_001357.1, GI:9626069), HPV 33 (Genbank Acc. No: M12732.1, GI:333049), HPV 35 (Genbank Acc. No: M74117.1, GI:333050), HPV 52 (Genbank Acc. No: X74481.1 GI:397038), or HPV 58 (Genbank Acc. No: D90400.1 GI:222386). It is also known that HR-HPVs can cause vulvar, anal, vaginal, penile and oropharyngeal cancer, as well as vaginal intraepithelial neoplasia, anal intraepithelial neoplasia, vulvar intraepithelial neoplasia, and penile intraepithelial neoplasia.

The HPV genome usually is single molecule of double stranded, circular closed DNA. E.g., the HPV16 genome consists of a single molecule of double-stranded, circular closed DNA with approximately 7,906 base pairs (see. e.g. Myers, G., H. Delius, J. Icenogle, H. U. Bernard, M. Favre, M. van Ranst, and C. M. Wheeler. 1997. Human papillomaviruses 1997: a compilation and analysis of nucleic acid and amino acid sequences. Theoretical Biology and Biophysics, Los Alamos National Laboratory, Los Alamos, N. Mex.). Three open reading frames (ORF) are located on one strand. Three functional areas have been defined, the long control region (LCR), and the "early" and the "late" transcription regions. The LCR is an 850 bp long non-coding upstream region responsible for the regulation of DNA replication and transcription. It contains several binding sites for the viral E2 and other cellular transcription factors and a binding site for the viral E1 replication protein. Furthermore, it contains silencer as well as enhancer sequences and harbours the p97 core promoter close to the E6 ORF; it is the region of the highest degree of variation in the viral genome. The "early" region, consists of the ORF E1, E2, E4, E5, E6 and E7, which are involved in viral replication and cell transformation. The "late" region encodes the L1 and L2 structural proteins that form the viral capsid. Of the "early" proteins, the two most important HPV proteins for malignant diseases are E6 and E7, which act synergistically to transform cells from normal to immortal state. It is known in the art that the HPV transcriptoms exhibit several splice donor (e.g. at nucleotide positions 226, 880, 1302 and 3632 of the HPV16R reference genome) and splice acceptor sites (e.g. at nucleotide positions 409, 526, 742, 2582, 2709, 3358 and 5639 of the HPV16R reference genome) resulting in at least 11 different splice junctions (Baker, C., and C. Calef. 1996. Maps of papillomavirus mRNA transcripts. Los Alamos National Laboratories, Los Alamos, N. Mex., USA.; Zheng, Z. M., and C. C. Baker. 2006. Papillomavirus genome structure, expression, and post-transcriptional regulation. Front Biosci 11:2286-302.). Splicing products are characterized herein based on the splice donor and acceptor sites used for generating the products. The respective splice donor and acceptor are separated by "^".

It is known in the art that infection with HR-HPV can be subclassified in various manifestations. Cervical cancer develops from areas of persistent HR-HPV infection through a series of well-defined stages that are histologically classified as cervical intraepithelial neoplasia 1 to 3 (CIN1 to CIN3). The stages of HR-HPV progression are also cytologically known as low- and high-grade squamous intraepithelial lesions (LSIL and HSIL). LSIL is equivalent to CIN1, whereas CIN2 and CIN3, preferably, are equivalent to HSIL. Initial infection with HPV16 can lead to the development of CIN1 which is manifested by inhibition of normal differentiation in the lower third of the epithelium. The majority of these lesions regress spontaneously in immunocompetent individuals, probably mediated by cellular immunity. However, in some individuals there is a risk, e.g. due to inherited or induced immune deficiencies that the infection with HR-HPV persists and that CIN1 lesions progress to a CIN2 lesion. A CIN2 lesion also shows a high regression rate, however, a CIN2 lesion may also progress to a high-grade disease (CIN3) which may progress to carcinoma (carcinoma in situ or even invasive) carcinoma.

The "mild form of HR-HPV infection" as meant herein, preferably, refers to a form of HR-HPV infection that is histologically classified as normal cervical tissue or as CIN1 (minimal or mild cervical dysplasia), or cytologically classified as NIL/M (negative for intraepithelial lesions or malignancy) or as LSIL (low-grade squamous intraepithelial lesions). Thus, the mild form of HR-HPV infection, preferably, encompasses benign cervical lesions, and, thus, mild grade HR-HPV lesions (for a review see Smith, J. H. 2002. Bethesda 2001. Cytopathology 13:4-10).

A "severe form of HR-HPV infection" as meant herein, preferably, refers to a form of HR-HPV infection that is histologically classified as CIN2 (moderate cervical epithelial dysplasia) or CIN3 (severe cervical dysplasia) or cancer (in situ or invasive). Accordingly, the term "severe form of HR-HPV infection" preferably, refers to a form of HR-HPV infection that is cytologically classified as HSIL or cancer. Thus, the severe form of HR-HPV infection, preferably, encompasses malign cervical lesions, and, thus, high-grad HR-HPV lesions (for a review see Smith, J. H. 2002. Bethesda 2001. Cytopathology 13:4-10).

A sample can be obtained by well known techniques and include samples from those cells, tissues or organs which express or produce the gene products referred to herein. Preferably, the samples are scrapes or biopsies from the urogenital or the oropharyngeal tract. Such samples can be obtained by use of brushes, (cotton) swabs, spatula, rinse/wash fluids, punch biopsy devices, puncture of cavities with needles or surgical instrumentation. Preferably, the scrapes contain mucosal cells. More preferably, the sample is a cervical smear or Pap smear. Separated cells may be obtained from the body fluids or the tissues or organs by separating techniques such as filtration, centrifugation or cell sorting. Moreover, the sample may be further processed by well known methods in order to further enrich and/or purify the gene products as referred to herein. The further processing of a gene product, preferably, depends on the nature of the gene product, i.e. whether the gene product is a polypeptide or an RNA molecule. Preferably, if the gene product is a polypeptide, then polypeptides are enriched and/or purified by methods well known by the skilled person. Preferably, if the gene product is an mRNA molecule, then said RNA molecules may enriched and/or purified by methods well known in the art.

The term "gene product" as used herein, preferably, relates to a transcript, and thus to mRNA, or to a polypeptide.

The gene product of E1C, preferably, is a transcript from the E1 gene isolated from a sample from an individual affected with a severe form of HR-HPV infection which has been spliced to comprise a splice junction which has a splice donor site at a position between positions 800 and 1000, preferably between positions 850 and 950 of the HPV genome, and a splice acceptor site between positions 2400 and 2900, preferably between positions 2500 and 2800 of the HPV genome. Preferably, the product of E1C is a transcript from the E1 gene which has been spliced to comprise a deletion of 1500 to 2100, preferably 1600 to 2000, or more preferably 1700 to 1900 nucleotides of the 5' part of the E1 gene, more preferably between the positions described supra. More preferably, the gene product is a spliced transcript comprising a 929^2779 junction of HPV18, a spliced transcript comprising a 894^2702 junction of HPV33, a spliced transcript comprising a 883^2649 junction of HPV35, a spliced transcript comprising a 879^2696 junction of HPV52, or a spliced transcript comprising a 898^2706 junction of HPV58. Most preferably the gene product is a spliced transcript comprising the 929^2779 junction of HPV18 comprised in a sequence as shown in SEQ ID NO: 1, comprising the 894^2702 junction of HPV33 comprised in a sequence as shown in SEQ ID NO: 2, comprising the 883^2649 junction of HPV35 comprised in a sequence as shown in SEQ ID NO: 3, comprising the 879^2696 junction of HPV52 comprised in a sequence as shown in SEQ ID NO: 25, or comprising the 898^2706 junction of HPV58 comprised in a sequence as shown in SEQ ID NO: 26 (Table 1).

TABLE 1

E1C splice junctions, proteins and preferred probes for HPV18, HPV33, and HPV35
All Sequences are shown as DNA sequences as they are obtained by sequencing. Nonetheless, the splice donor and splice acceptor sequences as well as the sequences comprising the splice junctions are comprised in RNA in the cell. The person skilled in the art knows how to transcribe DNA sequences to RNA sequences.

| HPV | Reference genome | E1C splice junction in reference genome | Splice donor | Splice acceptor | sequence comprising splice junction | Probe sequence |
|---|---|---|---|---|---|---|
| 18 | NC_001357.1 (SEQ ID NO: 13) | 929^2779 | TGATCCAGAAG (SEQ ID NO: 4) | GACATGGTCCAGA (SEQ ID NO: 7) | TGATCCAGAAGGACATGGTCCAGA (SEQ ID NO: 1) | AGAAGGACAT (SEQ ID NO: 10) |

TABLE 1-continued

E1C splice junctions, proteins and preferred probes for HPV18, HPV33, and HPV35
All Sequences are shown as DNA sequences as they are obtained by sequencing. Nonetheless,
the splice donor and splice acceptor sequences as well as the sequences comprising the
splice junctions are comprised in RNA in the cell. The person skilled in the art knows
how to transcribe DNA sequences to RNA sequences.

| HPV | Reference genome | E1C splice junction in reference genome | Splice donor | Splice acceptor | sequence comprising splice junction | Probe sequence |
|---|---|---|---|---|---|---|
| 33 | M12732.1 (SEQ ID NO: 14) | 894^2702 | CGATCCTGAAG (SEQ ID NO: 5) | GACGTGGTGCAAA (SEQ ID NO: 8) | CGATCCTGAAGGACGTGGTGCAAA (SEQ ID NO: 2) | TGAAGGACGT (SEQ ID NO: 11) |
| 35 | M74117.1 (SEQ ID NO: 15) | 883^2649 | TGATCCTGCAG (SEQ ID NO: 6) | GACGTGGTGCAGA (SEQ ID NO: 9) | TGATCCTGCAGGACGTGGTGCAGA (SEQ ID NO: 3) | TGCAGGACGT (SEQ ID NO: 12) |
| 52 | X74481.1 (SEQ ID NO: 32) | 879^2696 | GGACCCTGAAG (SEQ ID NO: 27) | GACGTGGTGC (SEQ ID NO: 29) | GGACCCTGAAGGACGTGGTGC (SEQ ID NO: 25) | TGAAGGACGT (SEQ ID NO: 11) |
| 58 | D90400.1 (SEQ ID NO: 33) | 898^2706 | TGACCCTGAAG (SEQ ID NO: 28) | GACGTGGTGCAAA (SEQ ID NO: 30) | TGACCCTGAAGGACGTGGTGCAAA (SEQ ID NO: 26) | CTGAAGGACGT (SEQ ID NO: 31) |

It is, however, also contemplated that the gene product of E1C is a polypeptide translated from said spliced transcripts of the E1 gene. Preferably, the gene product of E1C is a polypeptide comprising the amino acid sequence madpeghgpd for HPV18 (SEQ ID NO: 22), madpegrgan for HPV33 (SEQ ID NO: 23), madpagrgad for HPV35 (SEQ ID NO: 24), medpegrgan for HPV52 (SEQ ID NO: 34), or mddpegrgan for HPV 58 (SEQ ID NO: 35). More preferably, the gene product of E1C is a peptide consisting of the amino acid sequence madpeghgpd for HPV18 (SEQ ID NO: 22), madpegrgan for HPV33 (SEQ ID NO: 23), madpagrgad for HPV35 (SEQ ID NO: 24), medpegrgan for HPV52 (SEQ ID NO: 34), or mddpegrgan for HPV 58 (SEQ ID NO: 35).

The term "amount" as used herein encompasses the absolute amount of a gene product, the relative amount or concentration of the said gene product as well as any value or parameter which correlates thereto or can be derived there from. Such values or parameters comprise intensity signal values from all specific physical or chemical properties obtained from the said gene product by direct measurements. Moreover, encompassed are all values or parameters which are obtained by indirect measurements specified elsewhere in this description. E.g. for polypeptides response levels can be determined from biological read out systems in response to the peptides or intensity signals obtained from specifically bound ligands. It is to be understood that values correlating to the aforementioned amounts or parameters can also be obtained by all standard mathematical operations.

Preferably, determining the amount of polynucleotides or amplification products referred to in this invention relates to measuring the amount or concentration, preferably semi-quantitatively or quantitatively. Preferably, the determination includes a normalization step for the quantification of transcripts. Exemplarily, this normalization process will be briefly described for NASBA target amplification method. Normalization and thus quantification is preferably achieved by adding a predefined amount of calibrator RNA (Q-RNA) to the amplification mixture. Said calibrator RNA, preferably, shall be in vitro-transcribed RNA that can be amplified by the same oligonucleotides that are capable of specifically amplifying the transcripts to be analyzed. However, said Q-RNAs shall comprise a specific target region for a probe oligonucleotide (i.e. a target region not comprised by the transcript to be analyzed). Said specific target region shall allow for differentiating between the amplification product of the transcript to be analyzed and the amplification product of the Q-RNA. The principle of the normalization is the competitive co-amplification of Q-RNA and the mRNA to be analyzed with the same oligonucleotide pair (van Gemen et al. 1993: Quantification of HIV-1 RNA in plasma using NASBA during HIV-1 primary infection. J Virol Methods 43:177-87). It is to be understood that Q-RNA amounts, preferably, need to be titrated for each mRNA to be analyzed in the context of the present invention. For quantification expression levels can be compared to a standard curve using in vitro transcribed mRNA or to suitable reference material. This can be done by the skilled person without further ado.

The term "determining the presence or absence of a gene product" is understood by the skilled person. As used herein the term, preferably, relates to assessing whether a gene product is absent or present in a sample. Preferably, the presence of a gene product of E1C in a sample from a subject indicates that said subject su7ffers from a severe from of HR-HPV infection. Preferably, the absence of a gene product of E1C in a sample from a subject in a sample indicates that said subject suffers from a mild form of HPV infection.

Assessing whether a gene product is present or absent in a sample can be done by well known methods. E.g., if the number of molecules of a gene product is below detection limit, it will be concluded that the gene product is absent; if said number of molecules is above the detection limit, it will be concluded that the gene product is present in the sample. It is to be understood that the detection limit may depend on the type of detection system used; e.g. in PCR-based assays one molecule of a transcript may be detected, whereas in an ELISA assay several polypeptide molecules may be necessary to provide a detectable signal. The person skilled in the art knows how to adjust the detection system employed for maximum sensitivity and reliability, including inclusion of appropriate controls. The method used for determination of the amount of a gene product depends on the nature of the gene product, i.e. whether the gene product is a transcript or a polypeptide.

Determining the presence of the absence of a gene product in a sample can also be done by determining the amount of a the gene product in said sample and comparing the, thus determined amount to a reference amount. Determination of the amount of a transcript, and thus the amount of an mRNA, in a sample of a subject can be done by any method deemed appropriate. Preferably, the amount of a transcript is determined by using a probe oligonucleotide that specifically detects the transcript to be analyzed. All methods for determining the amount of a transcript could also be used to determine the presence or absence of a gene product, as described herein above.

The determination of the amount of a transcript or an amplification product thereof, by specific probe oligonucleotides, preferably, comprises the step of hybridizing a transcript or an amplification product (for an explanation of "amplification products", see below) thereof with probe oligonucleotides that specifically bind to the transcript or the amplification product thereof. A probe oligonucleotide in the context of the present invention, preferably, is a single-stranded nucleic acid molecule that is specific for said transcript or the amplification product thereof. The skilled person knows that a probe oligonucleotide comprises a stretch of nucleotides that specifically hybridizes with the target and, thus, is complementary to the target polynucleotide. Said stretch of nucleotides is, preferably, 85%, 90%, 95%, 99% or more preferably 100% identical to a sequence region comprised by a target polynucleotide.

In order to allow specific detection of a transcript or amplification product thereof, the probe oligonucleotide, preferably, specifically binds to the transcript or amplification product to be detected, but not to other polynucleotides comprised by said sample. How to choose suitable probe oligonucleotides is known in the art.

Examples for sequences suitably comprised in probe oligonucleotides for detecting splice junctions are shown in Table 1 ("Probe sequences", SEQUENCE ID NOs: 10, 11, 12, and 31). It is to be understood that said sequence suitably comprised is identical for HPV33 and HPV52; the person skilled in the art knows how to add extensions to probe oligonucleotides in order to obtain probe oligonucleotides specifically hybridizing with a given sequence, e.g. either hybridizing specifically to the E1C transcript of HPV33 or to the E1C transcript of HPV52, in case differentiation between the E1C transcript of HPV33 and the E1C transcript of HPV52 is desired. Increase of specificity of probe oligonucleotides for detecting E1C transcripts is obtained by extending probe sequences at the 5' and or 3' side, preferably on both sides. Most preferably, said probe sequences are located at or close to the center of probe oligonucleotides for detecting E1C transcripts. The person skilled in the art knows how add extensions to probe sequences in order to obtain probe oligonucleotides specifically hybridizing with a given sequence.

The probe oligonucleotides of the present invention may be labelled or contain other modifications including enzymes which allow a determination of the amount of a transcript or an amplification product thereof. Labelling can be done by various techniques well known in the art and depending of the label to be used. Preferred labels are described elsewhere in this specification.

The probe oligonucleotide may be bound to a solid surface or present in a liquid phase. As an example, the probe oligonucleotides are bound to a carrier providing a solid surface. Preferably, said carrier is a small particle or bead. The overall size of a small particle or bead, preferably, may be in the micrometer or nanometer range. Said beads and particles may be stained with a specific dye, more preferably with a specific fluorescent dye. Preferably, by staining various carriers with various dyes, the carries can be distinguished from each other. By using a carrier with a specific dye for a specific probe oligonucleotide (thus, a nucleic acid that targets the amplified polynucleotides of a specific sequence), said carrier is distinguishable from other carriers comprising different dyes. In one preferred embodiment commercially available Luminex microspheres (Luminex Corp., Austin, Tex., USA) are used. Thus, for detection of a transcript or amplification product thereof, the probes are coupled to fluorescence-labelled polystyrene beads (Luminex suspension array technology) which are hybridized with the amplification products under suitable, preferably, stringent conditions. Moreover, the amplification products may be identified by use of microarrays, Reverse-Line Blots (RLB), Dot blots or similar technologies which contain specific oligonucleotides linked to a suitable carrier. Probe oligonucleotides present in a liquid phase may bind to immobilised target nucleic acid molecules or amplified polynucleotides. Specific labels or modifications known by persons skilled in the art may allow target detection or signal amplification. In addition, amplification products may be detected by size separation e.g. gel or capillary electrophoresis, by nucleotide composition, using e.g. Nuclear Magnetic Resonance, or by real-time and signal amplification methods as described elsewhere herein.

The person skilled in the art is able to select suitable probe oligonucleotides. For the determination of spliced transcripts, it is particularly contemplated to determine the amount of said alternatively spliced mRNAs by using probe oligonucleotides that specifically bind to the nucleotides flanking the splice junction, and, thus bind the nucleic acid sequence that is generated by connecting the respective specific splice donor and splice acceptor nucleotide.

Preferably, the determination of the amount of a transcript comprises the steps of amplifying the said transcript with oligonucleotides that specifically amplify said transcript and determining the amount of the, thus, amplified transcripts. Thus, for determination of the amount of a transcript, it is particularly preferred to amplify the transcript by suitable methods described elsewhere herein, and then to determine the amount of the amplification product. Alternatively, the determination of the amount of a transcript is achieved by signal amplification methods with oligonucleotide probes that specifically bind said transcript and allow linear signal amplification and subsequent determination of the amplified signal.

An oligonucleotide for the amplification of transcripts in the context of the present invention shall comprise a number of nucleotides being sufficient for specific binding to a sequence stretch of a target polynucleotide. Preferably, an oligonucleotide as meant herein has between 15 and 40 nucleotides in length, more preferably between 18 and 30 nucleotides in length, and most preferably between 20-27 nucleotides in length. A probe oligonucleotide in the context of the present invention allows detection of a transcript as referred to herein and/or amplification products of said transcript (see elsewhere herein). By detecting a transcript or an amplification product thereof, the amount of a specific transcript can be assessed in a sample of a subject with HPV16. In order to allow specific detection of a transcript or an amplification product thereof, the probe oligonucleotide has to be sufficiently complementary to the transcript or amplification product thereof, or to parts of said transcript or said amplification product. Particularly preferred oligonucleotides have the specific sequences and/or properties referred to herein.

Particularly, the oligonucleotides may be biotinylated in order to enable the binding of the amplification products to a streptavidin surface or fluorescent conjugate. Moreover, labels to be used in the context of the present invention may be, but are not limited to, fluorescent labels comprising, inter alia, fluorochromes such as R-phycoerythrin, Cy3, Cy5, fluorescein, rhodamin, Alexa, or Texas Red. However, the label may also be an enzyme or an antibody. It is envisaged that an enzyme to be used as a label will generate a detectable signal by reacting with a substrate. Suitable enzymes, substrates and techniques are well known in the art. An antibody to be used as label may specifically recognize a target molecule which can be detected directly (e.g., a target molecule which is itself fluorescent) or indirectly (e.g., a target molecule which generates a detectable signal, such as an enzyme). Moreover, the oligonucleotides may contain generic sequences that allow detection by hybridisation to complementary detector probes that may contain any of the aforementioned labels or modifications. The oligonucleotides of the present invention may also contain 5'-restriction sites, locked nucleic acid molecules (LNA) or be part of a peptide nucleic acid molecule (PNA). Such PNA can be, in principle, detected via the peptide part by, e.g., antibodies.

How to amplify a transcript is well known in the art. Amplification of a transcript, preferably, is a template-dependent process which results in an increase of the amount of a corresponding nucleic acid molecule relative to the initial amounts. The amplification product, preferably, is a nucleic acid, DNA or RNA. It is to be understood that amplification of a transcript may comprise additional steps such as reverse transcription of the transcript by well known methods.

How to amplify a target signal is well known in the art. Amplification of a signal, preferably, is a template-dependent process which results in an increase of the amount of a reporter signal relative to the initial amounts. The reporter signal, preferably, is a visible light, fluorescence, chemiluminescence, and luminescence. Methods for signal amplification are well-known in the art and may be based on tyramide signal amplification, branched DNA amplification, Dendrimer® amplification, padlock probes and rolling circle amplification, Invader® signal amplification and other signal amplification methods.

The amplification of a transcript of interest may be carried out by well-known methods, preferably by polymerase chain reaction (PCR), by reverse transcriptase (RT) PCR, real-time PCR, nucleic acid sequence-based amplification (NASBA), transcription-mediated amplification (TMA) and other isothermal amplification methods using enzymes and specific oligonucleotides as primers. PCR methods are well known in the art. Preferably, the amplification is by using suitable oligonucleotides pairs.

The current invention is not restricted to any of the aforementioned technologies. As an exemplary method for the amplification of transcripts, NASBA technology will be briefly summarised. NASBA is an oligonucleotide-dependent technology for the amplification of nucleic acids at one temperature. The sample comprising the transcript to be amplified is added to a reaction mixture comprising at least two transcript specific oligonucleotides for the amplification of said transcript. The first oligonucleotide, containing the T7 RNA promoter sequence, binds to its target site at the 3' end of the template. By reverse transcription a RNA/DNA hybrid is generated. The enzyme RNAse H degrades the RNA portion. After degradation of the RNA template, the second oligonucleotide binds to the 3'-end of the single-stranded cDNA and double-stranded DNA containing an intact T7 RNA promoter is generated. Then, the enzyme T7 RNA polymerase linearly generates antisense RNA. Each newly synthesized antisense RNA molecule can itself act as a template with the second primer and is converted to a DNA intermediate with a functional T7 promoter. However, in this case the oligonucleotide primers anneal in reverse order because the newly generated RNA molecules are opposite in orientation to the original target and the resulting DNA intermediate is only partly double-stranded. In this manner, many RNA copies are generated from each RNA target that re-enter the reaction resulting in the linear synthesis of RNA products under isothermal conditions. An approximately $10^6$- to $10^9$-fold amplification is obtained within 90 min (Compton, J. 1991. Nucleic acid sequence-based amplification. Nature 350:91-2).

In order to specifically amplify spliced mRNAs as referred to herein, the oligonucleotide pair for the amplification of the transcript, preferably, shall be capable to specifically amplify the nucleic acid region that comprises the respective splicing junction. Therefore, the oligonucleotides for the amplification shall specifically bind the transcript (or the complementary strand thereof, particularly a complementary DNA or RNA strand that is generated by approaches described elsewhere herein) 5' and 3' from the splicing junction (one primer 3', one primer 5'). An amplification product generated by using the aforementioned oligonucleotides will comprise the respective splice junction. It is, however, also contemplated by the current invention that one oligonucleotide of the oligonucleotide pair specifically binds to the region of the E1C transcript comprising the splicing junction, such that specific binding, and thus amplification, can only occur if said E1C transcript is present in the sample. In such case, the absence of a transcript of the expected length is diagnostic for the absence of said transcript, and, thus, of a mild form of HR-HPV infection.

Determining the amount of polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a polypeptide can be achieved by all known means for determining the amount of a peptide in a sample. Said means comprise immunoassay devices and methods which may utilize labelled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Determination of the amount of a polypeptide, preferably, comprises the use of antibodies that specifically bind to the polypeptide to be determined. Preferably, if the polypeptide to be determined is derived from the translation of a specifically spliced HR-HPV transcript, then the antibody specifically shall bind to the region of the polypeptide that is encoded by the nucleic acids flanking the splice junction. Preferred antibodies are described elsewhere herein.

The term "reference amount" is a threshold value used to determine if an HR-HPV infection is a severe or a mild infection. If the amount of gene product of E1C determined in a sample exceeds the reference amount, the HR-HPV infection is severe; if the amount of gene product of E1C determined in a sample is equal or lower than the reference amount, the HR-HPV infection is mild. The skilled person knows how to determine the reference amount, e.g. by determining the amount of gene product of E1C in a representative set of samples where the severity of HR-HPV infection has been assessed (e.g. by the Pap-test) and using statistical analysis of the results obtained to determine the reference amount. It is to be understood that the reference amount can be zero.

The definitions made above apply mutatis mutandis to the following:

In a further embodiment, the current invention relates to a method for differentiating in a subject with HR-HPV between (i) a severe form of HR-HPV infection and (ii) a mild form of HR-HPV infection, comprising the steps a) determining the amount of a first gene product in a sample of said subject, said first gene product being a gene product of E1C, b) determining the amount of a second gene product in said sample, c) calculating a ratio of the amount of said first gene product as determined in step a) and the amount of said second gene product as determined in step b), d) comparing the ratio as calculated in step c) to a reference ratio, and e) differentiating between (i) a severe form of HR-HPV infection and (ii) a mild form of HR-HPV infection.

Preferably, the aforementioned method comprises the calculation of ratios of the amount of a gene product of E1C and a reference amount. A reference amount according to the invention is the amount of a second gene product, wherein the amount of said second gene product is known not to increase in cases of severe HR-HPV infection, as it is e.g. the case for cellular housekeeping genes, or e.g. the gene products of E1^E4, L1, or E5, expression of which either is constant or is decreased in severe HR-HPV-infection. As set forth herein above, the determination of the amount of a gene product of E1C (or a polypeptide encoded by the said spliced mRNA) is particularly advantageous for differentiating between mild and severe forms of HR-HPV infection.

The second gene product in the context of the aforementioned method of the present invention, preferably, is selected from the group consisting of, a gene product of E1^4, a gene product of Apm1, a gene product of Ubc, a gene product of U1A, a gene product of E1, a gene product of E5, a gene product of L1, and a gene product of E6*I.

The gene products of E1^E4 and of E6*I preferably, are alternatively spliced mRNAs of HR-HPV or polypeptides encoded by said alternatively spliced mRNAs. The splice sites of said alternatively spliced mRNAs are summarized in table 2.

TABLE 2

Splice junctions for the E1^E4 and
E6*I transcripts of HPV 18, 33, 35, 52, and 58.

| HPV | E1^E4 splice junction | E6*I splice junction |
| --- | --- | --- |
| HPV 18 | 929^3434 | 233^416 |
| (SEQ ID NO: 13) | (Meyers et al.) | (Pim et al.) |
| HPV 33 | 894^3351 | 231^509 |
| (SEQ ID NO: 14) | (Snijders et al.) | (Sotlar et al.) |
| HPV 35 | 883^3298 | 232^415 |
| (SEQ ID NO: 15) | (this specification) | (Sotlar et al.) |
| HPV 52 | 879^3345 | 224^502 |
| (SEQ ID NO: 32) | (this specification) | (Sotlar et al.) |
| HPV 58 | unknown* | 232^510 |
| (SEQ ID NO: 33) |  | (Sotlar et al.) |

*The exact position of the E1^E4 slice junction is determined according to the methods described in the references.

(References: —Sotlar K, Stubner A, Diemer D, et al. Detection of high-risk human papillomavirus E6 and E7 oncogene transcripts in cervical scrapes by nested RT-polymerase chain reaction. Journal of medical virology 2004; 74: 107-16.

Pim D, Massimi P, Banks L. Alternatively spliced HPV-18 E6* protein inhibits E6 mediated degradation of p53 and suppresses transformed cell growth. Oncogene 1997; 15:257-64.

Meyers C, Mayer T J, Ozbun M A. Synthesis of infectious human papillomavirus type 18 in differentiating epithelium transfected with viral DNA. J Virol 1997; 71:7381-6.

Snijders P J, van den Brule A J, Schrijnemakers H F, Raaphorst P M, Meijer C J, Walboomers J M. Human papillomavirus type 33 in a tonsillar carcinoma generates its putative E7 mRNA via two E6* transcript species which are terminated at different early region poly(A) sites. J Virol 1992; 66:3172-8.)

The term "gene product of E1^E4" as used herein, preferably, refers to RNAs corresponding to 880^3358 spliced mRNAs of HPV16, preferably transcripts comprising a 929^3434 splice junction of HPV18 or transcripts comprising a 894^3351 splice junction of HPV33; or the term relates to polypeptides encoded by said transcripts corresponding to the 880^3358 spliced mRNA of HPV16, said polypeptides preferably being a fusion polypeptides of the N-terminus of the E1 polypeptide with the E4 polypeptide of HPV. Said polypeptides are expressed in the late phase of the viral life cycle. They are detected in the spinous and granular cell layers and have several functions late in infection of HPV.

The term "gene product of E6*I" as used herein, preferably, refers mRNAs corresponding to 226^409 spliced mRNAs of HPV16, preferably transcripts comprising a 233^416 splice junction of HPV18, transcripts comprising a 231^509 splice junction of HPV33, or transcripts comprising a 232^415 splice junction of HPV33; or the term relates to polypeptides encoded by said transcripts corresponding to the 226^409 spliced mRNAs of HPV16. It has been suggested that E6*I polypeptide may transactivate the virus LCR (Alloul, N., and L. Sherman. 1999. Transcription-modulatory activities of differentially spliced cDNAs encoding the E2 protein of human papillomavirus type 16. J Gen Virol 80 (Pt 9):2461-70.).

Ubc, U1A, and Apm1 are genes that are comprised by the genome of the host cell. Thus, said genes are not encoded by the genome of HPV16. In the context of the present invention, the genes that are host-specific are also referred to as cellular genes. Gene products of Ubc, U1A and Apm1, preferably, are mRNAs and polypeptides encoded by the said genes. The method of the present invention, thus, contemplates the determination of the amount of the Ubc, U1A and Apm1 mRNAs or the Ubc, U1A and Apm1 polypeptides.

The term "Ubc" as meant herein, preferably, refers to ubiquitin C, preferably, human ubiquitin C. The nucleic acid sequence as well as the amino acid sequence of human Ubc1 are well known in the art and shown e.g. in GenBank Accession No: NM_021009.4 (nucleic acid sequence, SEQ ID NO: 16) and GenBank Accession No: NP_066289.2 (amino acid sequence, SEQ ID NO: 17).

The term U1A as meant herein, preferably, refers to U1 small nuclear ribonucleoprotein polypeptide A, preferably, human U1 small nuclear ribonucleoprotein polypeptide A. The nucleic acid sequence as well as the amino acid sequence of human U1A are well known in the art and shown e.g. in GenBank Accession No: NM_004596.3 (nucleic acid sequence, SEQ ID NO: 18) and GenBank Accession No: NP_004587.1 (amino acid sequence, SEQ ID NO: 19).

The term Apm1 as meant herein, preferably, refers to "Affected by Papillomavirus DNA integration in ME180 cells" or "zinc finger and BTB domain containing 7C" (ZBTB7C). The nucleic acid sequence as well as the amino acid sequence of human Apm1 are well known in the art and shown e.g. in GenBank Accession No: NM_001039360.1 (nucleic acid sequence, SEQ ID NO: 20) and GenBank Accession No: NP_001034449.1 (amino acid sequence, SEQ ID NO: 21).

The method of the present invention also contemplates the determination of the amount of the polynucleotides comprising the E1 transcript or the determination of the amount of the E1 polypeptide. Said polynucleotides and said polypeptide are encoded by the HR-HPV genome.

The E1 polypeptide is encoded by an unspliced E1 ORF (open reading frame)-containing transcript. E1 is essential for viral replication and shares structural similarities with the SV40 large tumour antigen. E1 exhibits ATPase, helicase and nucleotide-binding activities, interacts with the cellular DNA-polymerase α and recruits the cellular replication initiation machinery to the viral origin of replication in the LCR.

The method of the present invention also contemplates the determination of the amount of the polynucleotides comprising the E5 transcript or the determination of the amount of the E5 polypeptide. Said polynucleotides and said polypeptide are encoded by the HR-HPV genome.

The E5 polypeptide is expressed from an unspliced E2/E5 transcript but not from the E1^E4/E5 transcript. Upon integration of the HPV genome into the host genome, E5 polypeptide and transcript expression ceases due to disruption of the E2 region. E5 is a hydrophobic membrane protein that is found in intracellular membranes and the plasma membrane. The E5 dimer is thought to be important in the early course of infection as it interacts with growth factor receptors, EGF- or PDGF-receptor, and causes their ligand-independent dimerisation followed by trans-phosphorylation of cytosolic tyrosine residues and recruitment of cellular signal transduction proteins.

The method of the present invention also contemplates the determination of the amount of the polynucleotides comprising L1 transcript or the determination of the amount of the L1 polypeptide. Said polynucleotides and said polypeptide are encoded by the HR-HPV genome.

As set forth above, the L1 polypeptide of HPV is a capsid protein. During late stages of the productive infection the major capsid protein, the L1 polypeptide is expressed in differentiated cells near the top of the epithelium and forms with L2 polypeptide of HPV16 the viral capsids in the granular layer.

The term "comparing" as used herein encompasses comparing the value determined by calculating a ratio of the amount of a first gene product as determined in step a) of the method of the present invention and the amount of said second gene product as determined in step b) of the method of the present invention to a suitable reference source specified elsewhere in this description. It is to be understood that comparing as used herein refers to a comparison of values. The comparison referred to in step d) of the methods of the present invention may be carried out manually or computer-assisted. For a computer-assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the ratio calculated in step c) of the methods of the present invention to a reference ratio it is possible to differentiate, in a subject with HR-HPV, between a mild form of infection with HR-HPV and a severe form of infection with HR-HPV. Therefore, the reference ratio is to be chosen so that either a difference or a similarity in the compared values allows for differentiating between a mild form of infection with HPV16 and a severe form of infection with HPV.

Accordingly, the term "reference ratio" as used herein, preferably, refers to a value which allows differentiation between a mild form and a severe form of HR-HPV infection. Accordingly, the reference may be derived from carrying out steps a) and b) of the methods of the present invention and calculating a ratio of the amount of a first gene product, in a sample of a subject with HR-HPV infection, as determined in step a) of the method of the present invention, and the amount of said second gene product as determined in step b) of the method of the present invention, said subject being known to suffer from a severe form of HR-HPV infection such as HSIL or cervical cancer. Also, the reference may be derived from carrying out steps a) and b) of the methods of the present invention and calculating a ratio of the amount of a first gene product, in a sample of a subject with HR-HPV infection, as determined in step a) of the methods of the present invention and the amount of said second gene product, in a sample of a subject with HR-HPV in a subject, as determined in step b) of the methods of the present invention, said subject being known to show exhibit a mild form of HR-HPV infection (e.g. a form classified as LSIL). Suitable reference ratios or thresholds may be determined by the method of the present invention from a reference sample to be analyzed together, i.e. simultaneously or subsequently, with the test sample. It is to be understood that the value of the reference ratio or threshold may vary depending on the nature of the gene product (transcript or polypeptide) and depending on how the amount of a gene product is determined in the sample. For example, if the determination of the amount of the first and the second gene product includes amplification of the gene product by PCR, the determined amount of a gene product may depend, e.g., on the oligonucleotides used for the PCR reaction since the amplification efficiency of various oligonucleotide pairs for the amplification of a specific gene product varies. However, the person skilled in the art considers this when calculating the reference ratio. Particularly, the person skilled knows that, preferably, the same means and methods have to be used for determining the amounts of a specific gene product in a reference sample and in a test sample.

A reference amount for a marker as set forth herein or a reference ratio in the context of the present invention can be easily established. Moreover, an amount of a marker in a test sample or ratio of two markers in a test sample from a subject can simply be compared to the reference ratio and the reference amount, respectively. The sensitivity and specificity of a diagnostic test depends on more than just the analytical "quality" of the test—they also depend on the definition of what constitutes an abnormal result. In practice, Receiver Operating Characteristic curves, or "ROC" curves, are typically calculated by plotting the value of a variable versus its relative frequency in a population suffering from a mild form of HPV infection and a population suffering from a severe form of HPV infection. For any particular marker or ratio of markers, a distribution of marker levels or ratios of markers for subjects will likely overlap. Under such conditions, a test does not absolutely distinguish patients with a mild form of HPV infection from patients with a severe form of HPV infection with 100% accuracy, and the area of overlap indicates where the test cannot distinguish patients with a mild form of HPV infection from patients with a severe form of HPV infection. A threshold is selected, above which the test is considered as indicating a severe and below which the test is considered as indicating fibrosis. The area under the ROC curve is a measure of the probability that the perceived measurement will allow correct diagnosis of a subject. These methods are well known in the art. See, e.g., Hanley et al, Radiology 143: 29-36 (1982).

In certain embodiments, a reference amount/ratio selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In particularly preferred embodiments, both the sensitivity and specificity are at least about 75%, more preferably at least about 80%, even more preferably at least about 85%, still more preferably at least about 90%, and most preferably at least about 95%.

As set forth above, a reference may preferably, obtained from a sample from a subject to suffer from a severe form of HPV infection or a subject known to suffer from a mild form of HPV infection. The reference can also be the average or mean obtained from a group of such samples. The reference results may be obtained by applying the method of the present invention. The absolute or relative amounts of the biomarker(s) of said individuals of the population can be determined as specified elsewhere herein. How to calculate a suitable reference value or ratio, preferably, the average or median, is well known in the art. The population of subjects referred to before shall comprise a plurality of subjects, preferably, at least 5, 10, 50, 100, 1,000 or 10,000 subjects. It is to be understood that the subject to be assessed by the method of the present invention and the subjects of the said plurality of subjects are of the same species.

It is further contemplated that a "reference" will be obtained by determining the amount of a biomarker or the ratio of two biomarkers in a group of reference subjects, i.e. a group of subjects known to suffer from a severe form of HPV infection, or a group of subjects known to suffer from a mild form of HPV infection, and calculating the reference by appropriate statistic measures including those referred to elsewhere herein, such as median, average, quantiles, PLS-DA, logistic regression methods, random forest classification or others that give a threshold value. The threshold value should take the desired clinical settings of sensitivity and specificity of the test into consideration.

It is also envisaged that the assessment whether a subject suffers from a severe form of HPV infection or a mild form of HPV infection can be carried out on the degree of identity or similarity between the test results obtained from the test sample and the aforementioned reference results, i.e. based on an identical or similar amount with respect to a biomarker. For example, if the reference sample has been obtained from a subject suffering from a mild form of HPV infection and if the amount of a biomarker or if the ratio in a test sample is similar or identical to the amount of said biomarker or to the ratio in reference sample, then the presence of mild form of HPV infection can be diagnosed. The results of the test sample and the reference results are identical, if the values for the characteristic features and, in the case of quantitative determination, the intensity values are identical. Said results are similar, if the values/ratios of the characteristic features are identical but the intensity values/ratios are different. Such a difference is, preferably, not significant and shall be characterized in that the values for the intensity are within at least the interval between $1^{st}$ and $99^{th}$ percentile, $5^{th}$ and $95^{th}$ percentile, $10^{th}$ and $90^{th}$ percentile, $20^{th}$ and $80^{th}$ percentile, $30^{th}$ and $70^{th}$ percentile, $40^{th}$ and $60^{th}$ percentile of the reference value, the $50^{th}$, $60^{th}$, $70^{th}$, $80^{th}$, $90^{th}$ or $95^{th}$ percentile of the reference value.

It is also contemplated in the context of the method of the present invention, that the assessment may be based on differences between the test results obtained from the test sample and the aforementioned reference results. The same applies if a calculated reference as specified above is used. The difference, preferably, shall be an increase or a decrease with respect to a ratio as set forth herein or with respect to the absolute or relative amount of a diagnostic marker according to present invention. Preferably, the increase or decrease in the relative or absolute amount is significant, i.e. outside of the interval between $45^{th}$ and $55^{th}$ percentile, $40^{th}$ and $60^{th}$ percentile, $30^{th}$ and $70^{th}$ percentile, $20^{th}$ and $80^{th}$ percentile, $10^{th}$ and $90^{th}$ percentile, $5^{th}$ and $95^{th}$ percentile, $1^{st}$ and $99^{th}$ percentile of the reference value.

A preferred reference ratio serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques.

Preferably, the ratio calculated in the context of the present invention is the ratio of the amount of the first gene product to the amount of the second gene product. It is to be understood, that also the ratio of the amount of the second gene product to the first gene product can be calculated.

If the ratio of the amount of the first gene product to the amount of the second gene product is calculated, preferably, the following applies:

Preferably, a calculated ratio in the test sample larger than the reference ratio indicates a severe form of HR-HPV infection. More preferably, a calculated ratio in the test sample significantly larger than the reference ratio indicates a severe form of HR-HPV infection. Most preferably, a calculated ratio in the test sample that is statistically significantly larger than the reference ratio indicates a severe form of HR-HPV infection.

Preferably, a calculated ratio in the test sample lower than the reference ratio indicates a mild form of HR-HPV infection. More preferably, a calculated ratio in the test sample significantly lower than the reference ratio indicates a mild form of HR-HPV infection. Most preferably, said calculated ratio is statistically significantly lower than the reference ratio.

Particularly, a ratio significantly larger (or lower) or statistically significantly larger (or lower) than a reference ratio is a ratio of a size which is considered to be significant for the differentiation referred to herein. The terms "larger", "significantly larger", and "statistically significantly larger", "lower", "significantly lower", and "statistically significantly lower" are known by the person skilled in the art. Thus, whether a ratio is larger (or lower), significantly larger (or lower) or statistically significantly larger (or lower) can be determined without further ado by the person skilled in the art using various well known statistic evaluation tools.

In a further embodiment, the current invention relates to a device for differentiating in a subject with HR-HPV between (i) a severe form of HR-HPV infection and (ii) a mild form of HR-HPV infection, comprising means for determining the presence and/or amount of a gene product of E1C, and means for comparing said amount to a reference amount, allowing differentiating between (i) a severe form of HR-HPV infection and (ii) a mild form of HR-HPV infection.

Moreover, the present invention relates to a device for differentiating in a subject with HR-HPV between (i) a severe form of HR-HPV infection and (ii) a mild form of HR-HPV infection, comprising a detection agent for determining the presence and/or amount of a gene product of E1C allowing differentiating between (i) a severe form of HR-HPV infection and (ii) a mild form of HR-HPV infection.

Preferably, said device further comprises means for comparing the amount of a gene product of E1C to a reference amount.

The present invention also envisages a device for differentiating in a subject with HR-HPV between (i) a severe form of HR-HPV infection and (ii) a mild form of HR-HPV infection, comprising a detection agent for determining the amount of a first gene product in a sample of said subject, said first gene product being a gene product of E1C, a detection agent for determining the amount of a second gene product in said sample, means for calculating a ratio of the amount of said first gene product and the amount of said second gene product, means for comparing said ratio to a reference ratio, and means differentiating between (i) a severe form of HR-HPV infection and (ii) a mild form of HR-HPV infection.

Moreover, the present invention envisages a device adapted for carrying out the methods of the present invention disclosed above comprising:
a) an analyzing unit comprising a detection agent which specifically binds to a gene product of E1C, adapted for determining the amount and/or presence of a gene product of E1C, and, preferably,
b) an evaluation unit for comparing said amount with a reference amount, whereby it can be differentiated in a subject with HR-HPV between (i) a severe form of HR-HPV infection and (ii) a mild form of HR-HPV infection, said unit comprising a database with at least one reference ratio derived from a subject suffering from mild form of HR-HPV infection or derived from a subject suffering from a severe form of HR-HPV infection, and a computer-implemented algorithm for carrying out the comparison.

The present invention also pertains to a device adapted for carrying out the methods of the present invention disclosed above comprising:
a) an analyzing unit comprising a detection agent which specifically binds to a first gene product, said first gene product being a gene product of E1C, adapted for determining the amount of said first gene product and, preferably, a detection agent which specifically binds to a second gene product adapted for determining the amount of said second gene product; and
b) an evaluation unit for calculating a ratio of the amount of the said first and said second gene product, and for comparing said ratio with a reference ratio, whereby it can be differentiated in a subject with HR-HPV between (i) a severe form of HR-HPV infection and (ii) a mild form of HR-HPV infection, said unit comprising a database with at least one reference ratio derived from a subject suffering from mild form of HR-HPV infection or derived from a subject suffering from a severe form of HR-HPV infection, and a computer-implemented algorithm for carrying out a comparison.

Preferred gene products of E1C as well as second gene products are specified elsewhere herein. Preferably, the HR-HPV and the corresponding gene product of E1C are
a) HPV18 and a spliced transcript comprising a 929^2779 junction,
b) HPV33 and a spliced transcript comprising a 894^2702 junction,
c) HPV35 and a spliced transcript comprising a 883^2649 junction,
d) HPV52 and a spliced transcript comprising a 879^2696 junction, or
e) HPV58 and a spliced transcript comprising a 898^2706 junction.

The term "device" as used herein relates to a system comprising the aforementioned units operatively linked to each other as to allow the diagnosis or monitoring according to the methods of the invention. The term "detection agent" as used herein refers to an agent which is capable of specifically recognizing and binding to the gene product present in a sample. Preferred detection agents (such as probes or antibodies, oligonucleotides which specifically amplify transcripts) are disclosed in detail elsewhere herein. The determined amount and/or the presence or the absence of a gene product can be transmitted to the evaluation unit. Said evaluation unit comprises a data processing element, such as a computer, with an implemented algorithm for carrying out a comparison between the determined amount and a suitable reference. Suitable references are either derived from a subject suffering from a mild form of HR-HPV infection or from a subject suffering from a severe form of HR-HPV infection as described elsewhere herein. The results may be given as output of parametric diagnostic raw data, preferably, as absolute or, more preferably, relative amounts. It is to be understood that these data will need interpretation by the clinician. However, also envisage are expert system devices wherein the output comprises processed diagnostic raw data the interpretation of which does not require a specialized clinician.

Further encompassed by the present invention is a kit, preferably adapted to carry out the methods of the present invention, comprising instructions to carry out the said method, said kit further comprising a detection agent for determining the presence and/or amount of a gene product of E1C, and, preferably, means for comparing said amount to a reference amount, allowing differentiating between (i) a severe form of HR-HPV infection and (ii) a mild form of HR-HPV infection.

The present invention also pertains to a kit preferably adapted to carry out the methods of the present invention, comprising instructions to carry out the said method, said kit further comprising a detection agent for determining the amount of a first gene product in a sample of said subject, said first gene product being a gene product of E1C, a detection agent for determining the amount of a second gene product in said sample, means for calculating a ratio of the amount of said first gene product and the amount of said second gene product, means for comparing said ratio to a reference ratio, and means differentiating between (i) a severe form of HR-HPV infection and (ii) a mild form of HR-HPV infection.

Preferred gene products of E1C as well as second gene products are specified elsewhere herein. Preferably, the HR-HPV and the corresponding gene product of E1C are
a) HPV18 and a spliced transcript comprising a 929^2779 junction,
b) HPV33 and a spliced transcript comprising a 894^2702 junction,
c) HPV35 and a spliced transcript comprising a 883^2649 junction,
d) HPV52 and a spliced transcript comprising a 879^2696 junction, or
e) HPV58 and a spliced transcript comprising a 898^2706 junction.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device.

In a further preferred embodiment, the current invention relates to a transcript of a HR-HPV genome comprising a splice junction, wherein the combination of HR-HPV and splice junction are selected from the list consisting of a) HPV18 and a 929^2779 junction, b) HPV33 and a 894^2702 junction, c) HPV35 and a 883^2649 junction, d) HPV52 and a 879^2696 junction, and HPV58 and a 898^2706 junction.

Moreover, the current invention relates to a mixture of oligonucleotides comprising i) at least one first oligonucleotide specifically hybridizing to the splice junction of an E1C transcript and ii) at least one second oligonucleotide specifically hybridizing to a transcript selected from the group consisting of a transcript of E6*I, a transcript of E1^E4, a transcript of Apm1, a transcript of Ubc, a transcript of U1A, a transcript of E1, a transcript of E5, and a transcript of L1.

Furthermore, this invention relates to an antibody, specifically recognizing a peptide having a sequence as shown in SEQ ID NO: 22, 23, 24, 34, or 35. Preferably, said antibody specifically recognizes at least 5, 6, 7 or 8 contiguous amino acids of the peptide having a sequence as shown in SEQ ID NO: 22, 23, 24, 34, or 35.

Antibodies against the polypeptides of the invention can be prepared from suitable fragments of a purified polypeptide according to the invention as an antigen. Such fragments may be obtained either from the polypeptide of the invention by proteolytic digestion or may be a synthetic peptide. Preferably, the antibody of the present invention is a monoclonal antibody, a polyclonal antibody, a single chain antibody, a human or humanized antibody or primatized, chimerized or fragment thereof. Also comprised as antibodies by the present invention are a bispecific antibody, a synthetic antibody, an antibody fragment, such as Fab, Fv or scFv fragments etc., or a chemically modified derivative of any of these. The antibody of the present invention shall specifically bind (i.e. does not cross react with other polypeptides or peptides) to the polypeptide of the invention. Specific binding can be tested by various well known techniques.

Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals.

The antibodies can be used, for example, for the immunoprecipitation and immunolocalization of the variant polypeptides of the invention as well as for the monitoring of the presence of or the amount of said polypeptides and for the identification of compounds interacting with the proteins according to the invention. For example, surface plasmon resonance as employed in the BIAcore system can be used to increase the efficiency of phage antibodies which bind to an epitope of the protein of the invention (Schier, Human Antibodies Hybridomas 7 (1996), 97-105; Malmborg, J. Immunol. Methods 183 (1995), 7-13).

All references cited in this specification are herewith incorporated by reference with respect to their entire disclosure content and the disclosure content specifically mentioned in this specification.

The following Example shall merely illustrate the invention. It shall not be construed, whatsoever, to limit the scope of the invention.

EXAMPLES

Example 1

Identification of HPV16-Analoguous E1C Transcripts in HR-HPV 18, 33, 35, 52, and 58

Cervical exfoliated cells from patients with low-grade to high-grade lesion or CxCa, stored in PreservCyt™ medium (ThinPrep sampling device), were selected for RNA isolation based on prior HPV18, 33, 35, 52, and 58 genotyping data. After vigorous homogenisation, 3 to 12 ml of cell suspension were transferred to a 15 ml Falcon tube and centrifuged for 10 min, 10° C., 4000 rpm (300×g). The supernatant was removed and the cell pellet was resuspended in the residual volume by flicking the tube. Absolute ethanol (2.5 ml) was added and the mixture was well homogenised by pipetting. 1.5 ml of the suspension was transferred in a 2 ml Eppendorf tube (not provided with the EZ1 RNA kit) centrifuged, and the supernatant was discarded, and stored at −80° C. RNA isolation was performed according to the manufacturer's instructions omitting DNase treatment.

Using the Qiagen one-step RT-PCR kit, newly designed forward and backward primers, annealing in the E7 and E2 gene, respectively, amplified a truncated PCR product that was detected only in total RNA from patients with high-grade lesions or CxCa. Upon cloning and sequencing, the respective splice junctions could be identified by sequencing.

The invention claimed is:

1. A method for assigning risk in a subject infected with HR-HPV, said subject not comprising the HR-HPV genome in an integrated form, comprising the steps of:
   a) determining in a sample of said subject the presence of a gene product of E1C, said gene product of E1C being a spliced transcript of E1 which has been spliced to comprise a splice junction which has a splice donor site at a position between positions 800 and 1000 and a splice acceptor site between positions 2400 and 2900, wherein the determining of said transcript comprises the steps of amplifying said transcript with oligonucleotides that specifically amplify said transcript and hybridizing said amplified transcript with a probe oligonucleotide that comprises SEQ ID NO 10, thereby detecting said splice junction and determining the presence of the amplified transcript-probe complex, and
   b) assigning said subject determined to have said gene product of E1C as having high risk of suffering from a severe form of HR-HPV infection.

2. The method of claim 1, wherein the HR-HPV is HPV18 and wherein the gene product of E1C is a transcript comprising a 929^2779 junction.

3. The method of claim 1, wherein determining the presence of the spliced transcript of E1C comprises PCR amplification of said spliced transcript of E1C.

4. The method of claim 3, wherein PCR amplification makes use of a mixture of primers.

5. The method of claim 1, comprising the further step of assessing in said sample of said subject the integration status of the HR-HPV genome.

6. A method for providing a risk stratification in a subject infected with HR-HPV, comprising the steps
   a) determining, the amount of a first gene product in a sample of said subject infected with HR-HPV, said first gene product being a gene product of E1C, said gene product of E1C being a spliced transcript of E1 which has been spliced to comprise a splice junction which has a splice donor site at a position between positions 800 and 1000, and a splice acceptor site between positions 2400 and 2900, wherein the determination of the amount of said transcript comprises the steps of amplifying said transcript with oligonucleotides that amplify said transcript and hybridizing said amplified transcript with a probe oligonucleotide comprising SEQ ID NO 10, detecting said splice junction within said transcript by forming an amplified transcript-probe complex, and determining the amounts of the amplified transcript-probe complex,
   b) assigning said subject to a group having a high risk of suffering from a severe form of HR-HPV infection, whereby said subject assigned to high risk requires further diagnosis for cervical diseases, including colposcopy,
   c) determining the amount of a second gene product in said sample,
   d) calculating a ratio of the amount of said first gene product as determined in step a) and the amount of said second gene product as determined in step c),
   e) comparing the ratio as calculated in step d) to a reference ratio, and
   f) differentiating between a severe form of HR-HPV infection and a mild form of HR-HPV infection, wherein an amount of the amplified transcript-probe complex indicating the presence of said spliced transcript of E1 in said sample indicates a severe form of HR-HPV infection.

7. The method of claim 6, wherein said second gene product is Ubc.

8. The method of claim 7, wherein the HR-HPV and the corresponding splice transcript of E1C are HPV18 and a spliced transcript comprising a 929^2779 junction.

9. The method of claim 6, wherein the ratio of the amount of said first gene product to the amount of said second gene product is calculated and wherein a ratio larger than the reference ratio indicates a severe form of HR-HPV infection.

10. The method of claim 6, comprising the further step of assessing in said sample of said subject the integration status of the HR-HPV genome.

11. A method for classifying a subject infected with HR-HPV as having increased risk of high grade squamous intraepithelial lesions (HSIL) or cervical cancer, said subject not comprising the HR-HP genome in an integrated form, comprising the steps
   a) determining, in a sample of said subject, the presence of a gene product of E1C, said gene product of E1C being a spliced transcript of E1 which has been spliced to comprise a splice junction which has a splice donor site at a position between positions 800 and 1000 and a splice acceptor site between positions 2400 and 2900, wherein the determination of the presence of said transcript comprises the steps of amplifying said transcript with oligonucleotides that specifically amplify said transcript and hybridizing said amplified transcript with a probe oligonucleotide comprising SEQ ID NO 10, thereby detecting said splice junction and determining the amounts of the amplified transcript-probe complex, and
   b) classifying said subject determined to have said splice junction with having increased risk of HSIL or cervical cancer.

* * * * *

```
                              SEQUENCE LISTING

<160> NUMBER OF SEQ ID NOS: 35

<210> SEQ ID NO 1
<211> LENGTH: 24
<212> TYPE: DNA
<213> ORGANISM: HPV18

<400> SEQUENCE: 1
tgatccagaa ggacatggtc caga                                              24

<210> SEQ ID NO 2
<211> LENGTH: 24
<212> TYPE: DNA
<213> ORGANISM: HPV33

<400> SEQUENCE: 2
cgatcctgaa ggacgtggtg caaa                                              24

<210> SEQ ID NO 3
<211> LENGTH: 24
<212> TYPE: DNA
<213> ORGANISM: HPV35

<400> SEQUENCE: 3
tgatcctgca ggacgtggtg caga                                              24

<210> SEQ ID NO 4
<211> LENGTH: 11
<212> TYPE: DNA
<213> ORGANISM: HPV18

<400> SEQUENCE: 4
tgatccagaa g                                                            11

<210> SEQ ID NO 5
<211> LENGTH: 11
<212> TYPE: DNA
<213> ORGANISM: HPV33

<400> SEQUENCE: 5
cgatcctgaa g                                                            11

<210> SEQ ID NO 6
<211> LENGTH: 11
<212> TYPE: DNA
<213> ORGANISM: HPV35

<400> SEQUENCE: 6
tgatcctgca g                                                            11

<210> SEQ ID NO 7
<211> LENGTH: 13
<212> TYPE: DNA
<213> ORGANISM: HPV18

<400> SEQUENCE: 7
gacatggtcc aga                                                          13
```

```
<210> SEQ ID NO 8
<211> LENGTH: 13
<212> TYPE: DNA
<213> ORGANISM: HPV33

<400> SEQUENCE: 8
gacgtggtgc aaa                                                          13

<210> SEQ ID NO 9
<211> LENGTH: 13
<212> TYPE: DNA
<213> ORGANISM: HPV35

<400> SEQUENCE: 9
gacgtggtgc aga                                                          13

<210> SEQ ID NO 10
<211> LENGTH: 10
<212> TYPE: DNA
<213> ORGANISM: HPV18

<400> SEQUENCE: 10
agaaggacat                                                              10

<210> SEQ ID NO 11
<211> LENGTH: 10
<212> TYPE: DNA
<213> ORGANISM: HPV33

<400> SEQUENCE: 11
tgaaggacgt                                                              10

<210> SEQ ID NO 12
<211> LENGTH: 10
<212> TYPE: DNA
<213> ORGANISM: HPV35

<400> SEQUENCE: 12
tgcaggacgt                                                              10

<210> SEQ ID NO 13
<211> LENGTH: 7857
<212> TYPE: DNA
<213> ORGANISM: HPV18

<400> SEQUENCE: 13
attaatactt ttaacaattg tagtatataa aaagggagt aaccgaaaac ggtcgggacc          60
gaaaacggtg tatataaaag atgtgagaaa cacaccacaa tactatggcg cgctttgagg        120
atccaacacg gcgaccctac aagctacctg atctgtgcac ggaactgaac acttcactgc        180
aagacataga ataacctgt gtatattgca agacagtatt ggaacttaca gaggtatttg        240
aatttgcatt taaagattta tttgtggtgt atagagacag tataccccat gctgcatgcc        300
ataaatgtat agattttat tctagaatta gagaattaag acattattca gactctgtgt        360
atggagacac attggaaaaa ctaactaaca ctgggttata caatttatta ataaggtgcc        420
tgcggtgcca gaaaccgttg aatccagcag aaaaacttag acaccttaat gaaaaacgac        480
gatttcacaa catagctggg cactatagag gccagtgcca ttcgtgctgc aaccgagcac        540
gacaggaacg actccaacga cgcagagaaa cacaagtata atattaagta tgcatggacc        600
taaggcaaca ttgcaagaca ttgtattgca tttagagccc caaaatgaaa ttccggttga        660
```

```
ccttctatgt cacgagcaat taagcgactc agaggaagaa acgatgaaa tagatggagt    720 taatcatcaa catttaccag cccgacgagc cgaaccacaa cgtcacacaa tgttgtgtat    780
gtgttgtaag tgtgaagcca gaattgagct agtagtagaa agctcagcag acgaccttcg    840
agcattccag cagctgtttc tgaacaccct gtcctttgtg tgtccgtggt gtgcatccca    900
gcagtaagca acaatggctg atccagaagg tacagacggg gagggcacgg gttgtaacgg    960
ctggttttat gtacaagcta ttgtagacaa aaaaacagga gatgtaatat cagatgacga   1020
ggacgaaaat gcaacagaca cagggtcgga tatggtagat tttattgata cacaaggaac   1080
attttgtgaa caggcagagc tagagacagc acaggcattg ttccatgcgc aggaggtcca   1140
caatgatgca caagtgttgc atgttttaaa acgaaagttt gcaggaggca gcacagaaaa   1200
cagtccatta ggggagcggc tggaggtgga tacagagtta agtccacggt tacaagaaat   1260
atctttaaat agtgggcaga aaaggcaaa aaggcggctg tttacaatat cagatagtgg   1320
ctatggctgt tctgaagtgg aagcaacaca gattcaggta actacaaatg gcgaacatgg   1380
cggcaatgta tgtagtggcg gcagtacgga ggctatagac aacgggggca cagagggcaa   1440
caacagcagt gtagacggta caagtgacaa tagcaatata gaaaatgtaa atccacaatg   1500
taccatagca caattaaaag acttgttaaa agtaaacaat aaacaaggag ctatgttagc   1560
agtatttaaa gacacatatg gctatcatt tacagattta gttagaaatt ttaaaagtga   1620
taaaaccacg tgtacagatt gggttacagc tatatttgga gtaaacccaa caatagcaga   1680
aggatttaaa acactaatac agccatttat attatatgcc catattcaat gtctagactg   1740
taaatgggga gtattaatat tagccctgtt gcgttacaaa tgtggtaaga gtagactaac   1800
agttgctaaa ggtttaagta cgttgttaca cgtacctgaa acttgtatgt taattcaacc   1860
accaaaattg cgaagtagtg ttgcagcact atattggtat agaacaggaa tatcaaatat   1920
tagtgaagta atgggagaca cacctgagtg gatacaaaga cttactatta tacaacatgg   1980
aatagatgat agcaatttttg atttgtcaga aatggtacaa tgggcatttg ataatgagct   2040
gacagatgaa agcgatatgg catttgaata tgccttatta gcagacagca acagcaatgc   2100
agctgccttt ttaaaaagca attgccaagc taaatattta aaagattgtg ccacaatgtg   2160
caaacattat aggcgagccc aaaaacgaca aatgaatatg tcacagtgga tacgatttag   2220
atgttcaaaa atagatgaag ggggagattg gagaccaata gtgcaattcc tgcgatacca   2280
acaaatagag tttataacat ttttaggagc cttaaaatca ttttttaaaag gaaccccaa   2340 aaaaaattgt ttagtatttt gtggaccagc aaatacagga aaatcatatt ttggaatgag   2400
ttttatacac tttatacaag gagcagtaat atcatttgtg aattccacta gtcatttttg   2460
gttggaaccg ttaacagata ctaaggtggc catgttagat gatgcaacga ccacgtgttg   2520
gacatacttt gatacctata tgagaaatgc gttagatggc aatccaataa gtattgatag   2580
aaagcacaaa ccattaatac aactaaaatg tcctccaata ctactaacca caaatataca   2640
tccagcaaag gataatagat ggccatattt agaaagtaga ataacagtat tgaatttcc   2700 aaatgcattt ccatttgata aaatggcaa tccagtatat gaaataatg acaaaaattg   2760 gaaatgtttt tttgaaagga catggtccag attagatttg cacgaggaag aggaagatgc   2820
agacaccgaa ggaaaccctt tcggaacgtt taagttgcgt gcaggacaaa atcatagacc   2880
actatgaaaa tgcacagtaaa gacatagaca gccaaataca gtattggcaa ctaatacgtt   2940
gggaaaatgc aatattcttt gcagcaaggg aacatggcat acagacatta aaccaccagg   3000
tggtgccagc ctataacatt tcaaaaagta aagcacataa agctattgaa ctgcaaatgg   3060
```

```
ccctacaagg ccttgcacaa agtcgataca aaaccgagga ttggacactg caagacacat    3120
gcgaggaact atggaataca gaacctactc actgctttaa aaaaggtggc caaacagtac    3180
aagtatattt tgatggcaac aaagacaatt gtatgaccta tgtagcatgg gacagtgtgt    3240
attatatgac tgatgcagga acatgggaca aaaccgctac ctgtgtaagt cacaggggat    3300
tgtattatgt aaaggaaggg tacaacacgt tttatataga atttaaaagt gaatgtgaaa    3360
aatatgggaa cacaggtacg tgggaagtac attttgggaa taatgtaatt gattgtaatg    3420
actctatgtg cagtaccagt gacgacacgg tatccgctac tcagcttgtt aaacagctac    3480
agcacacccc ctcaccgtat ccagcaccg tgtccgtggg caccgcaaag acctacggcc    3540
agacgtcggc tgctacacga cctggacact gtggactcgc ggagaagcag cattgtggac    3600
ctgtcaaccc acttctcggt gcagctacac ctacaggcaa caacaaaaga cggaaactct    3660
gtagtggtaa cactacgcct ataatacatt taaaaggtga cagaaacagt ttaaaatgtt    3720
tacggtacag attgcgaaaa catagcgacc actatagaga tatatcatcc acctggcatt    3780
ggacaggtgc aggcaatgaa aaaacaggaa tactgactgt aacataccat agtgaaacac    3840
aaagaacaaa atttttaaat actgttgcaa ttccagatag tgtacaaata ttggtgggat    3900
acatgacaat gtaatacata tgctgtagta ccaatatgtt atcacttatt ttttattttt    3960
gcttttgtgt atgcatgtat gtgtgctgcc atgtcccgct tttgccatct gtctgtatgt    4020
gtgcgtatgc atgggtattg gtatttgtgt atattgtggt aataacgtcc cctgccacag    4080
cattcacagt atatgtattt tgttttttat tgcccatgtt actattgcat atacatgcta    4140
tattgtcttt acagtaattg ataggttgt tttatacagt gtattgtaca ttgtatattt    4200
tgttttatac ctttttatgct ttttgtattt ttgtaataaa agtatggtat cccaccgtgc    4260
cgcacgacgc aaacgggctt cggtaactga cttatataaa acatgtaaac aatctggtac    4320
atgtccacct gatgttgttc ctaaggtgga gggcaccacg ttagcagata aaatattgca    4380
atggtcaagc cttggtatat ttttgggtgg acttggcata ggtactggca gtggtacagg    4440
gggtcgtaca gggtacattc cattgggtgg gcgttccaat acagtggtgg atgttggtcc    4500
tacacgtccc ccagtggtta ttgaacctgt gggccccaca gacccatcta ttgttacatt    4560
aatagaggac tccagtgtgg ttacatcagg tgcacctagg cctacgttta ctggcacgtc    4620
tgggtttgat ataacatctg cgggtacaac tacacctgcg gttttggata tcacaccttc    4680
gtctacctct gtgtctattt ccacaaccaa ttttaccaat cctgcatttt ctgatccgtc    4740
cattattgaa gttccacaaa ctggggaggt ggcaggtaat gtatttgttg gtaccccctac    4800
atctggaaca catgggtatg aggaaatacc tttacaaaca tttgcttctt ctggtacggg    4860
ggaggaaccc attagtagta ccccattgcc tactgtgcgg cgtgtagcag gtccccgcct    4920
ttacagtagg gcctaccaac aagtgtcagt ggctaaccct gagtttctta cacgtccatc    4980
ctctttaatt acatatgaca acccggcctt tgagcctgtg gacactacat taacatttga    5040
tcctcgtagt gatgttcctg attcagattt tatggatatt atccgtctac ataggcctgc    5100
tttaacatcc aggcgtgga ctgttcgctt tagtagatta ggtcaacggg caactatgtt    5160
tacccgcagc ggtacacaaa taggtgctag ggttcacttt tatcatgata taagtccttat    5220
tgcaccttcc ccagaatata ttgaactgca gcctttagta tctgccacgg aggacaatga    5280
cttgtttgat atatatgcag atgacatgga ccctgcagtg cctgtaccat cgcgttctac    5340
tacctccttt gcattttta aatattcgcc cactatatct tctgcctctt cctatagtaa    5400
tgtaacggtc cctttaacct cctcttggga tgtgcctgta tacacgggtc ctgatattac    5460
```

```
attaccatct actacctctg tatggcccat tgtatcaccc acggcccctg cctctacaca    5520
gtatattggt atacatggta cacattatta tttgtggcca ttatattatt ttattcctaa    5580
gaaacgtaaa cgtgttccct attttttttgc agatggcttt gtggcggcct agtgacaata   5640
ccgtatatct tccacctcct tctgtggcaa gagttgtaaa taccgatgat tatgtgactc    5700
ccacaagcat attttatcat gctggcagct ctagattatt aactgttggt aatccatatt    5760
ttagggttcc tgcaggtggt ggcaataagc aggatattcc taaggtttct gcataccaat    5820
atagagtatt tagggtgcag ttacctgacc caaataaatt tggtttacct gatactagta    5880
tttataatcc tgaaacacaa cgtttagtgt gggcctgtgc tggagtggaa attggccgtg    5940
gtcagccttt aggtgttggc cttagtgggc atccatttta taataaatta gatgacactg    6000
aaagttccca tgccgccacg tctaatgttt ctgaggacgt tagggacaat gtgtctgtag    6060
attataagca gacacagtta tgtattttgg gctgtgcccc tgctattggg gaacactggg    6120
ctaaaggcac tgcttgtaaa tcgcgtcctt tatcacaggg cgattgcccc cctttagaac    6180
ttaaaaacac agttttggaa gatggtgata tggtagatac tggatatggt gccatggact    6240
ttagtacatt gcaagatact aaatgtgagg taccattgga tatttgtcag tctatttgta    6300
aatatcctga ttatttacaa atgtctgcag atccttatgg ggattccatg ttttttttgct   6360 tacggcgtga gcagcttttt gctaggcatt tttggaatag agcaggtact atgggtgaca    6420
ctgtgcctca atccttatat attaaaggca caggtatgcc tgcttcacct ggcagctgtg    6480
tgtattctcc ctctccaagt ggctctattg ttacctctga ctcccagttg tttaataaac    6540
catattggtt acataaggca cagggtcata acaatggtgt tgctggcat aatcaattat     6600 ttgttactgt ggtagatacc actcccagta ccaatttaac aatatgtgct tctacacagt    6660
ctcctgtacc tgggcaatat gatgctacca aatttaagca gtatagcaga catgttgagg    6720
aatatgattt gcagtttatt tttcagttgt gtactattac tttaactgca gatgttatgt    6780
cctatattca tagtatgaat agcagtattt tagaggattg gaactttggt gttcccccc     6840 ccccaactac tagtttggtg gatacatatc gttttgtaca atctgttgct attacctgtc    6900
aaaaggatgc tgcaccggct gaaaataagg atccctatga taagttaaag ttttggaatg    6960
tggatttaaa ggaaaagttt tctttagact tagatcaata tccccttgga cgtaaatttt    7020
tggttcaggc tggattgcgt cgcaagccca ccataggccc tcgcaaacgt tctgctccat    7080
ctgccactac gtcttctaaa cctgccaagc gtgtgcgtgt acgtgccagg aagtaatatg    7140
tgtgtgtgta tatatatata catctattgt tgtgtttgta tgtcctgtgt ttgtgtttgt    7200
tgtatgattg cattgtatgg tatgtatggt tgttgttgta tgttgtatgt tactatattt    7260
gttggtatgt ggcattaaat aaaatatgtt ttgtggttct gtgtgttatg tggttgcgcc    7320
ctagtgagta acaactgtat tgtgtttgt ggtatgggtg ttgcttgttg ggctatatat     7380
tgtcctgtat ttcaagttat aaaactgcac accttacagc atccatttta tcctacaatc    7440
ctccattttg ctgtgcaacc gatttcggtt gcctttggct tatgtctgtg gttttctgca    7500
caatacagta cgctggcact attgcaaact ttaatctttt gggcactgct cctacatatt    7560
ttgaacaatt ggcgcgcctc tttggcgcat ataaggcgca cctggtatta gtcattttcc    7620
tgtccaggtg cgctacaaca attgcttgca taactatatc cactccctaa gtaataaaac    7680
tgcttttagg cacatatttt agtttgtttt tacttaagct aattgcatac ttggcttgta    7740
caactacttt catgtccaac attctgtcta cccttaacat gaactataat atgactaagc    7800
tgtgcataca tagtttatgc aaccgaaata ggttgggcag cacatactat acttttc       7857
```

<210> SEQ ID NO 14
<211> LENGTH: 7909
<212> TYPE: DNA
<213> ORGANISM: HPV33

<400> SEQUENCE: 14

| | | | | | |
|---|---|---|---|---|---|
| gtaaactata | atgccaagtt | ttaaaaaagt | agggtgtaac | cgaaagcggt | tcaaccgaaa | 60 |
| acggtgcata | tataaagcaa | acattttgca | gtaaggtact | gcacgactat | gtttcaagac | 120 |
| actgaggaaa | aaccacgaac | attgcatgat | ttgtgccaag | cattggagac | aactatacac | 180 |
| aacattgaac | tacagtgcgt | ggaatgcaaa | aaaccctttgc | aacgatctga | ggtatatgat | 240 |
| tttgcatttg | cagatttaac | agttgtatat | agagagggaa | atccatttgg | aatatgtaaa | 300 |
| ctgtgtttgc | ggttcttatc | taaaattagt | gaatatagac | attataatta | ttctgtatat | 360 |
| ggaaatacat | tagaacaaac | agttaaaaaa | cctttaaatg | aaatattaat | taggtgtatt | 420 |
| atatgtcaaa | gacctttgtg | tcctcaagaa | aaaaacgac | atgtggattt | aaacaaacga | 480 |
| tttcataata | tttcgggtcg | ttgggcaggg | cgctgtgcgg | cgtgttggag | gtcccgacgt | 540 |
| agagaaactg | cactgtgacg | tgtaaaaacg | ccatgagagg | cacaagcca | acgttaaagg | 600 |
| aatatgtttt | agatttatat | cctgaaccaa | ctgacctata | ctgctatgag | caattaagtg | 660 |
| acagctcaga | tgaggatgaa | ggcttggacc | ggccagatgg | acaagcacaa | ccagccacag | 720 |
| ctgattacta | cattgtaacc | tgttgtcaca | cttgtaacac | cacagttcgt | ttatgtgtca | 780 |
| acagtacagc | aagtgaccta | cgaaccatac | agcaactact | tatgggcaca | gtgaatattg | 840 |
| tgtgccctac | ctgtgcacaa | caataaacat | catctacaat | ggccgatcct | gaaggtacaa | 900 |
| atgggggctgg | gatggggtgt | actggttggt | ttgaggtaga | agcagtcata | gagagaagaa | 960 |
| caggagataa | tatttcagaa | gatgaggatg | aaacagcaga | tgacagtggc | acggatttac | 1020 |
| tagagtttat | agatgattct | atggaaaata | gtatacaggc | agacacagag | gcagcccggg | 1080 |
| cattgtttaa | tatacaggaa | ggggaggatg | atttaaatgc | tgtgtgtgca | ctaaaacgaa | 1140 |
| agtttgccgc | atgttcacaa | agtgctgcgg | aggacgttgt | tgatcgtgct | gcaaacccgt | 1200 |
| gtagaacgtc | tattaataaa | aataagaat | gcacatacag | aaaacgaaaa | atagatgagc | 1260 |
| tagaagacag | cggatatggc | aatactgaag | tggaaactca | gcagatggta | caacaggtag | 1320 |
| aaagtcaaaa | tggcgacaca | aacttaaatg | acttagaatc | tagtggggtg | ggggatgatt | 1380 |
| cagaagtaag | ctgtgagaca | aatgtagata | gctgtgaaaa | tgttacgttg | caggaaatta | 1440 |
| gtaatgttct | acatagtagt | aatacaaaag | caaatatatt | atataaattt | aaagaggcct | 1500 |
| atggaataag | ttttatggaa | ttagtaagac | catttaaaag | tgataaaaca | agctgtacag | 1560 |
| attggtgtat | aacaggatat | ggaattagtc | catcagtagc | agaaagttta | aaagtattaa | 1620 |
| ttaaacagca | tagtttgtat | actcatttac | aatgtttaac | ttgcgataga | ggaataataa | 1680 |
| tattattgtt | aattagattt | aggtgtagca | aaaacaggtt | aacagtagca | aaactaatga | 1740 |
| gtaatttatt | atcaatacct | gaaacatgta | tggttataga | gccaccaaaa | ttacggagcc | 1800 |
| aaacatgtgc | attgtattgg | tttagaacag | caatgtcaaa | cattagtgat | gtacaaggta | 1860 |
| caacacctga | atggatagat | agactaactg | ttttacaaca | tagctttaat | gataatatat | 1920 |
| ttgatttaag | tgaaatggta | cagtgggcat | atgataacga | gttaacggac | gatagtgaca | 1980 |
| ttgcatatta | ttatgcacaa | cttgcagatt | caaatagtaa | tgctgctgca | ttttttaaaa | 2040 |
| gtaactcaca | agcaaaaata | gtaaaggact | gtggaataat | gtgtagacat | tataaaaaag | 2100 |
| cagaaaaacg | taaaatgtca | ataggacaat | ggataaaag | tagatgtgaa | aaaacaaatg | 2160 |

-continued

```
atggaggaaa ttggagacca atagtacagt tgttaagata tcaaaacatt gaatttacag    2220
cattttagg  tgcatttaaa aagttttaa  aaggtatacc aaaaaaaagc tgtatgctaa     2280
tttgtggacc agcaaataca ggaaagtcat attttggaat gagtttaata cagttttaa     2340
aagggtgtgt tatatcatgt gtaaattcta aaagtcactt ttggttgcag ccattatcag    2400
atgcaaaaat aggaatgata gatgatgtaa cgccaataag ttggacatat atagatgatt    2460
acatgagaaa tgcgttagat ggaaatgaaa tttcaataga tgtgaaacat agggcattag    2520
tgcaattaaa atgtccacca ctgcttctta cctcaaatac aaatgcaggc acagactcta    2580
gatggccata tttacatagt agattaacag tatttgaatt taaaaatcca ttcccatttg    2640
atgaaaatgg taacccagtg tatgcaataa atgatgaaaa ttggaaatcc ttttctcaa     2700
ggacgtggtg caaattagat ttaatagagg aagaggacaa ggaaaccat  ggaggaaata    2760
tcagcacgtt taaatgcagt gcaggagaaa atactagatc tttacgaagc tgataaaact    2820
gatttaccat cacaaattga acattggaaa ctgatacgca tggagtgtgc tttattgtat    2880
acagccaaac aaatgggatt ttcacattta tgccaccagg tggtgccttc tttgttagca    2940
tcaaagacca aagcatttca agtaattgaa ctacaaatgg cattagagac attaagtaaa    3000
tcacagtata gtacaagcca atggacattg caacaaacaa gcttagaggt gtggctttgt    3060
gaaccaccaa aatgttttaa aaaacaagga gaaacagtaa ctgtgcaata tgacaatgac    3120
aaaaaaaata caatggatta tacaaactgg ggtgaaatat atattataga ggaagataca    3180
tgtactatgg ttacagggaa agtagattat ataggtatgt attatataca taactgtgaa    3240
aaggtatatt ttaaatattt taagaggat  gctgcaaagt attctaaaac acaaatgtgg    3300
gaagtacatg tgggtggtca ggtaattgtt tgtcctacgt ctatatctag caaccaaata    3360
tccactactg aaactgctga catacagaca gacaacgata accgaccacc acaagcagcg    3420
gccaaacgac gacgacctgc agacaccaca gacaccgccc agccccttac aaagctgttc    3480
tgtgcagacc ccgccttgga caatagaaca gcacgtactg caactaactg cacaaacaag    3540
cagcggactg tgtgtagttc taacgttgca cctatagtgc atttaaaagg tgaatcaaat    3600
agtttaaaat gtttaagata cagattaaaa ccttataaag agttgtatag ttctatgtca    3660
tccacctggc attggaccag tgacaacaaa aatagtaaaa atggaattgt aactgtaaca    3720
tttgtaactg aacagcaaca acaaatgttt ttaggtaccg taaaaatacc acctactgtg    3780
caaataagta ctggatttat gacattataa gtgtacatca caagccaata tgtgctgcta    3840
attgtatata accatgatat ttgttttttgt attatgtttt atattgtttt tatgcttatc    3900
cttattatta cgtcctttaa tactttccat ttctacctat gcttggttgc tggtgttggt    3960
attgctgctt tgggtgtttg tgggatctcc tttaaaaatt ttttttttgct atttgttgtt    4020
tttatattta ccaatgatgt gtattaattt tcatgcacag catatgacac aacaagagta    4080
atgtatatac atgtatatat tgtttgtata tatgtgcaca tggtggtgtt ttaacattgt    4140
tgttgttatt ttagtttttt tttttttgta ttactaataa ataccttat  attttagcag    4200
tgtattatta tgagacacaa acgatctaca aggcgcaagc gtgcatctgc aacacaacta    4260
taccaaacat gcaaggccac aggcacctgc ccacccgatg ttattcctaa agtgaagga     4320
agtaccatag cagatcaaat tcttaaatat ggcagtttag gggttttttt tggtggttta    4380
ggtattggca caggctctgg ttcaggtgga aggactggct atgtacctat tggtactgac    4440
ccacctacag ctgcaatccc cttgcagcct atacgtcctc cggttactgt agacactgtt    4500
ggacctttag actcgtctat agtgtcatta atagaagaaa caagttttat agaggcaggt    4560
```

```
gcaccagccc catctattcc tacaccatca ggttttgatg ttactacatc tgcagatact    4620
acacctgcaa ttattaatgt ttcatctgtt ggggagtcat ctattcaaac tatttctaca    4680
catttaaatc ccacatttac tgaaccatct gtactacacc ctccagcgcc tgcagaagcc    4740
tctggacatt ttatattttc ttcccctact gttagcacac aaagttatga aaacatacca    4800
atggatacct ttgttgtttc cacagacagt agtaatgtaa catcaagcac gcccattcca    4860
gggtctcgcc ctgtggcacg ccttggttta tatagtcgca atacccaaca ggttaaggtt    4920
gttgaccctg ctttttttaac atcgcctcat aaacttataa catatgataa tcctgcattt    4980
gaaagctttg accctgaaga cacattacaa tttcaacata gtgatatatc acctgctcct    5040
gatcctgact ttctagatat tattgcatta cataggcctg ctattacatc tcgtagacat    5100
actgtgcgtt ttagtagagt aggtcaaaaa gccacactta aaactcgcag tggtaaacaa    5160
attggagcta gaatacatta ttatcaggat ttaagtccta ttgtgccttt agaccacacc    5220
gtgccaaatg aacaatatga attacagcct ttacatgata cttctacatc gtcttatagt    5280
attaatgatg gtttgtatga tgtttatgct gacgatgtgg ataatgtaca caccccaatg    5340
caacactcat acagtacgtt tgcaacaaca cgtaccagca atgtgtctat acctttaaat    5400
acaggatttg atactcctgt tatgtctggc cctgatatac cttcccttt atttcccaca    5460 tctagcccat ttgttcctat ttcgcctttt tttccttttg acaccattgt tgtagacggt    5520
gctgactttg ttttacatcc tagttatttt attttacgtc gcaggcgtaa acgttttcca    5580 tatttttttta cagatgtccg tgtggcggcc tagtgaggcc acagtgtacc tgcctcctgt    5640
acctgtatct aaagttgtca gcactgatga atatgtgtct cgcacaagca tttattatta    5700
tgctggtagt tccagacttc ttgctgttgg ccatccatat ttttctatta aaaatcctac    5760
taacgctaaa aaattattgg tacccaaagt atcaggcttg caatataggg tttttagggt    5820
ccgtttacca gatcctaata aatttggatt tcctgacacc tcctttata accctgatac    5880 acaacgatta gtatgggcat gtgtaggcct tgaaataggt agagggcagc cattaggcgt    5940
tggcataagt ggtcatcctt tattaaacaa atttgatgac actgaaaccg gtaacaagta    6000
tcctggacaa ccgggtgctg ataataggga atgtttatcc atggattata acaaacaca    6060 gttatgttta cttggatgta agcctccaac aggggaacat tggggtaaag gtgttgcttg    6120
tactaatgca gcacctgcca atgattgtcc acctttagaa cttataaata ctattattga    6180
ggatggtgat atggtggaca caggatttgg ttgcatggat tttaaaacat gcaggctaa    6240 taaaagtgat gttcctattg atatttgtgg cagtacatgc aaatatccag attatttaaa    6300
aatgactagt gagccttatg gtgatagttt attttttcttt cttcgacgtg aacaaatgtt    6360
tgtaagacac ttttttaata gggctggtac attaggagag gctgttcccg atgacctgta    6420
cattaaaggt tcaggaacta ctgcctctat tcaaagcagt gcttttttttc ccactcctag    6480 tggatcaatg gttacttccg aatctcagtt atttaataag ccatattggc tacaacgtgc    6540
acaaggtcat aataatggta tttgttgggg caatcaggta tttgttactg tggtagatac    6600
cactcgcagt actaatatga ctttatgcac acaagtaact agtgacagta catataaaaa    6660
tgaaaatttt aaagaatata taagacatgt tgaagaatat gatctacagt tgtttttca    6720 actatgcaaa gttaccttaa ctgcagaagt tatgacatat attcatgcta tgaatccaga    6780 tatttttagaa gattgcaat ttggtttaac acctcctcca tctgctagtt acaggatac    6840 ctataggttt gttacctctc aggctattac gtgtcaaaaa acagtacctc caaggaaaa    6900 ggaagacccc ttaggtaaat atacattttg ggaagtggat ttaaaggaaa aatttttcagc    6960
```

```
agatttagat cagtttcctt tgggacgcaa gtttttatta caggcaggtc ttaaagcaaa    7020
acctaaactt aaacgtgcag cccccacatc cacccgcaca tcgtctgcaa aacgcaaaaa    7080
ggttaaaaaa taacactttg tgtaattgtg ttatgttgtt gttttgttct gtctatgtac    7140
tttgtgttgt tgtgttgtgt tgttgtttgt ttttgtgta tgtgttacaa tgtatgttat    7200
gttgtatgtt actgtgtttg ttttatgtgt acttgtttgt gtgcatgttc tatgtacttg    7260
tcagtttcct gtttgtgtat atgttaataa aacattgtgt gtatttgtta aactatttgt    7320
atgtatgtta tgtatatggg tgtacctata tgagtaagga gttgtattgc ttgccctacc    7380
ctgcattgca atgtacctac ctttatttcc ctatatttgt agtacctaca tgtttagtat    7440
tgctttacct tttgacatac tagtgtccat attgtacaat ttcctccatt ttgtatgcct    7500
aaccgttttc ggttacttgg catacatacc ctatgacatt ggcagaacag ttaatccttt    7560
tctttcctgc actgtgtttg tctgtacttg ctgcattggc atacataccc tatgacattg    7620
gcagaacagt taatccttttt ctttcctgca ctgtgtttgt ctgtacttgc tgcattgact    7680
catatataca tgcagtgcaa ttgcaaaata cttaattgta ctaatagttt acacatgctt    7740
ttaggcacat attttactt tactttcaaa ccttaagtgc agttttggct tacacaattg    7800
ctttgtatgc caaactatgc cttgtaaaag tgagtcacta cctgtttatt accaggtgtg    7860
gactaaccgt tttaggtcat attggtcatt tataatcttt tatataata              7909
```

<210> SEQ ID NO 15
<211> LENGTH: 7851
<212> TYPE: DNA
<213> ORGANISM: HPV35

<400> SEQUENCE: 15

```
ccctataaaa aaaacaggga gtgaccgaaa acggtcgtac cgaaaacggt tgccataaaa      60
gcagaagtgc acaaaaaagc agaagtggac agacattgta aggtgcggta tgtttcagga     120
cccagctgaa cgaccttaca aactgcatga tttgtgcaac gaggtagaag aaagcatcca     180
tgaaatttgt ttgaattgtg tatactgcaa acaagaatta cagcggagtg aggtatatga     240
ctttgcatgc tatgatttgt gtatagtata tagagaaggc cagccatatg gagtatgcat     300
gaaatgttta aaatttttatt caaaaataag tgaatataga tggtatagat atagtgtgta     360
tggagaaacg ttagaaaaac aatgcaacaa acagttatgt catttattaa ttaggtgtat     420
tacatgtcaa aaaccgctgt gtccagttga aaagcaaaga catttagaag aaaaaaaacg     480
attccataac atcggtggac ggtggacagg tcggtgtatg tcctgttgga aaccaacacg     540
tagagaaacc gaggtgtaat catgcatgga gaaataacta cattgcaaga ctatgtttta     600
gatttggaac ccgaggcaac tgacctatac tgttatgagc aattgtgtga cagctcagag     660
gaggaggaag atactattga cggtccagct ggacaagcaa aaccagacac ctccaattat     720
aatattgtaa cgtcctgttg taaatgtgag gcgacactac gtctgtgtgt acagagcaca     780
cacattgaca tacgtaaatt ggaagattta ttaatgggca catttggaat agtgtgcccc     840
ggctgttcac agagagcata atctacaatg gctgatcctg caggtacaga tgaaggggag     900
gggacgggat gtaatggatg gttttttgta gaagcagtag ttagtagacg tacgggatcc     960
agtgtagagg acgaaaatga agatgactgt gacagggggg aggatatggt ggactttata    1020
aatgatacag atatattaaa catacaggca gaaacagaga cagcacaagc attatttcat    1080
gcacaggagg agcaaacaca caaagaggct gtacaggtcc taaaacgaaa gtatgctagt    1140
agtccactta gcagcgtgag cttatgtgtt aataataaca taagtccacg tttaaaagct    1200
```

```
atttgcattg aaaataaaaa tacagcagca aagcgacgat tatttgaact accagacagc    1260
ggttatggca attctgaagt ggaaatacac gagatacaac aggtagaggg gcatgataca    1320
gttgaacaat gtagtatggg cagtggggat agtataacct ctagtagcga tgaaagacat    1380
gatgagactc caacgcgaga cataatacaa atactaaaat gtagtaatgc aaacgcagct    1440
atgttggcta aatttaaaga actatttggt attagtttta cagaacttat tagaccattt    1500
aagagtgata aatccacatg tacagattgg tgtgtggccg catttggaat agccccaagt    1560
gtggcgaact ttaaacatat aacatatgta tacatataca atgtttatcg tgttcatggg    1620
gctatggtaa ttctagcatt attacgattt aaagtcgaaa aacgagaaca acaattgaaa    1680
actattgatg ctaaattgct atgtatttca gctgcaagta tgctaataca accaccaaaa    1740
ttacgtagta ccccagctgc gttatattgg tttaaaacag caatgtcaaa tattagtgag    1800
gttgatggag aaacaccaga atggattcaa agacaaacag tattacagca tagttttaat    1860
gatgcaatat ttgacctatc tgaaatggta caatgggcat atgacaatga ttttatagat    1920
gatagtgata tagcatataa atatgcacaa ttggcagaaa ctaatagtaa tgcatgtgct    1980 ttttttaaaaa gtaattcgca agctaaaatt gtaaaagatt gtgcaacaat gtgtagacat    2040
tataaacgag ctgaaaaaag agaaatgaca atgtcacagt ggattaaaag gcgatgtgca    2100
caggtggacg atgacggtga ctggagggac atagtacgat ttttaagata tcaacaagta    2160
gattttgtgg cattttttatc tgcactaaaa aatttttttac atggtgtgcc taaaaaaaat    2220
tgcatactaa tatatggagc accaaacaca ggtaaatcat tatttggaat gagtctaatg    2280
catttcttac aaggagctat tatatcctat gtaaattcta aaagccattt ttggttgcag    2340
ccattatatg atgccaaaat agctatgtta gatgatgcta catcgccatg tggcatatat    2400
agaccaatat ttaagaaatg cactagatgg aaatcctata tttcatttag atgtaaagca    2460
ttaagcatag tgcatataat gcccaccttt acttattaca tcaatataaa tgcaggcaaa    2520
gatgacaggt ggcctatactt acatagcagg gtagtggtct ttacatttca caatgaattc    2580
ccatttgata aaaatggaaa cccagagtat gggcttaatg ataaaaactg aaatcctttt    2640
ttctcaagga cgtggtgcag attaaatttg cacgaggaag aggtcaaaga aaatgatgga    2700
gacgctttcc cagcgtttaa gtgtgtgtca ggacaaaata ctagaacatt acgagactga    2760
tagcacatgt ttgtctgatc acatacagta ttggaaactg attcgtcttg aatgtgcagt    2820
attttataaa gcaagagaaa tgggaattaa aactcttaac caccaagtgg ttccaacgca    2880
ggccatttca aaagccaaag caatgcaagc aattgaactg caattaatgt tagagacatt    2940
aaatacaact gagtatagca cagaggactg gacactgcaa gaaacaagta ttgaactata    3000
tacaacagtt cctacaagat gtttaaaaaa agatgtttat actgtggaag cacaatttga    3060
tggtgataaa caaaatacta tgcattatac taattggaca catatatata tattagagga    3120
cagtatatgt actgttgtaa agggactggt aaattataaa ggtatttatt atgtgcatca    3180
gggtgtagaa acatattatg ttacttttag ggaagaggct aaaaagtatg aaaaaaaaa    3240 tatatgggaa gtgcatgtgg gtggtcaggt aattgtttgt cctgaatctg tatttagcag    3300
cacagaacta tccactgctg aaattgctac acagctacac gcctacaaca ccaccgagac    3360
ccataccaaa gcctgctccg tgggcaccac agaaacccag aagacaaatc acaaacgact    3420 tcgaggggt accgagctcc cctacaaccc caccaagcga gtgcgactca gtgccgtgga    3480
cagtgttgac agagggtgtct actctacatc tgactgcaca aacaaagacc ggtgtggtag    3540
ttgtagtaca actacaccta tagtacattt aaaaggtgat gcaaatacat aaagtgttc    3600
```

```
aagatataga ttgggtaaat ataaagcatt gtatcaagat gcttcatcta catggagatg    3660
gacatgtaca aacgataaaa aacaaatagc aattgtaaca ttaacttaca caacagaata    3720
tcaaagggat aaattttaa ctacagtaaa aatacctaac acagttacag tgtctaaagg     3780
atatatgtct atatgataga ccttacagct tccagtactg tgttgctgtg ctttttgttg    3840
tgcttttgtg tgcttttgtg cttgtgtctg cttgtacgtt cgctattgct atctgtgtca    3900
ttatactcag cattaatatt actggtttta atactgtggg ttactgtagc aacaccacta    3960
cttgcttttg ttgtttcttg cttttgtata tacctatgga tgattaacgc tcatgcacaa    4020
tatttggcag tacagtaatt gtatacaaac attgtgtttg gtactgtgta acatgtgtgt    4080
atggtggttt tattttttgt tgttcattgt atattttgtt tttttactgt ttttaaacat    4140
ttttatttct gtgtttttaa taaattgatc acatggtata accatgcgac acaaaaggtc    4200
tacaaaacgt gttaaacgtg catctgcaac acaactatat cgtacttgca aagctgcagg    4260
aacttgtcca ccagatgtta tacctaaggt tgagggtaat actgttgctg atcaaatttt    4320
aaaatatggc agcatggctg tgtttttgg ggggttagga attggttctg gatctggcac     4380
aggtggaaga tctggatatg ttccactggg tacaacacct ccaacggctg ccacaaacat    4440
tcctatacga cccctgtaa ctgtggaaag tataccatta gacacaattg gccctttaga     4500
ttcttctata gtgtcattag tagaggaaac tagttttatt gagtctggtg ccctgttgt     4560 tacaccaagg gtcccaccta caacaggttt tacaataacc acatctacag ataccacacc    4620
tgctatttta gatgtgacat ccataagtac acatgataat cctactttca ctgatccttc    4680
tgttttacac ccacccacgc ctgcagaaac ttcaggtcat tttgtacttt catcatcttc    4740
tattagtaca cataattatg aagaaatccc tatggatact tttattgttt ccacagacag    4800
caataatata actaatagca cgcctattcc agggtctcgc cctacgacac gcctaggatt    4860
atatagtaaa ggtacccagc aggttaaggt tgttgaccct gcctttatga cttctcctgc    4920
aaaacttatt acatatgata atcctgcata tgaaggcctt aaccctgata caaccttaca    4980
atttgagcat gaggatatta gcttagctcc ggatcctgac tttatggaca ttatagcttt    5040
acataggcct gcactaacat ctaggaaagg cactattaga tatagtagag taggtaataa    5100
acgtactatg catacacgaa gtggaaaagc tatagggca cgggtacatt attatcagga     5160
tttaagtagt attactgaag atatagaatt acaaccctta caacatgtac catcctcttt    5220
accacatacc actgtttcaa catcattaaa tgatggtatg tttgatattt atgctcctat    5280
agatactgag gaagatatta tattttcagc atcttctaac aatactttat atactacatc    5340
taacactgca tatgttccta gcaatactac tataccatta agtagtggct atgatattcc    5400
tataacagca gggccagaca ttgtatttaa ctctaatact attactaact ctgtactacc    5460
ggtacccaca ggtcctatat attctattat tgcagatggg ggtgactttt atttacaccc    5520
tagttattat ttattaaaac gacgtcgtaa agctatccca tatttttttg cagatgtctc    5580
tgtggcggtc taacgaagcc actgtctacc tgcctccagt gtcagtgtct aaggttgtta    5640
gcactgatga atatgtaaca cgcacaaaca tctactatca tgcaggcagt tctaggctat    5700
tagctgtggg tcacccatac tatgctatta aaaacaagga ttctaataaa atagcagtac    5760
ccaaggtatc tggtttgcaa tacagagtat ttagagtaaa attaccagat cctaataagt    5820
ttggatttcc agacacatca ttttatgatc cctgcctcca gcgtttggtt tgggcctgta    5880
caggagttga agtaggtcgt ggtcagccat taggagtagg tattagtggt catccttat     5940 taaataaatt ggatgatact gaaaatctta ataaatatgt tggtaactct ggtaactctg    6000
```

-continued

| | |
|---|---|
| gtacagataa cagggaatgc atttctatgg attataaaca aacacaattg tgtttaatag | 6060 |
| gttgtaggcc tcctataggt gaacattggg gaaaaggcac accttgtaat gctaaccagg | 6120 |
| taaaagcagg agaatgtcct cctttggagt tactaaacac tgtactacaa gacgggaca | 6180 |
| tggtagacac aggatttggt gcaatggatt ttactacatt acaagctaat aaaagtgatg | 6240 |
| ttcccctaga tatatgcagt tccatttgca aatatcctga ttatctaaaa atggtttctg | 6300 |
| agccatatgg agatatgtta tttttttatt tacgtaggga gcaaatgttt gttagacatt | 6360 |
| tatttaatag ggctggaact gtaggtgaaa cagtacctgc agacctatat attaagggta | 6420 |
| ccactggcac attgcctagt actagttatt ttcctactcc tagtggctct atggtaacct | 6480 |
| ccgatgcaca aatatttaat aaaccatatt ggttgcaacg tgcacaaggc cataataatg | 6540 |
| gtatttgttg gagtaaccaa ttgtttgtta ctgtagttga tacaacccgt agtacaaata | 6600 |
| tgtctgtgtg ttctgctgtg tcttctagtg acagtacata taaaaatgac aattttaagg | 6660 |
| aatatttaag gcatggtgaa gaatatgatt tacagtttat ttttcagtta tgtaaaataa | 6720 |
| cactaacagc agatgttatg acatatattc atagtatgaa cccgtccatt ttagaggatt | 6780 |
| ggaattttgg ccttacacca ccgccttctg gtaccttaga ggacacatat cgctatgtaa | 6840 |
| catcacaggc tgtaacttgt caaaaaccca gtgcaccaaa acctaaagat gatccattaa | 6900 |
| aaaattatac tttttgggag gttgatttaa aggaaaagtt ttctgcagac ttagatcagt | 6960 |
| ttccgttggg ccgtaaattt ttgttacaag caggactaaa ggccaggcct aattttagat | 7020 |
| taggcaggcg tgcagctcca gcatctacat ctaaaaaatc ttctactaaa cgtagaaaag | 7080 |
| taaaagtta atgtgtaaat gtgtatgcat gtatactgtg tgttatgtgt tgtagtgctt | 7140 |
| gtatatatat tatgtgttgt ggtgcctgtt tgtgttgtac atggcgtgta aatgtgtgta | 7200 |
| taatattgtg caatgtgttg tacgtgggtg ttttttgtact tagtgtgtag tagttcagta | 7260 |
| gccataaagt gatgtgtgtg tttataatta acactgtatt gttgtatgac tatggtgcac | 7320 |
| cgatatgagc ttacataatt acatgacagc tatattgtgt atataaataa tctacctcca | 7380 |
| ttttgtgtgt tagtgtccct tacattacct ttcaaccgat ttcggttgct gttggtaagc | 7440 |
| tttatatgtt ttttacaaaa acattcctac ctcagcagaa cacttaatcc ttgtgttcct | 7500 |
| gatatatatt gtttgccaac tttatattgg cttttgccaa tctttaaact tgattcatct | 7560 |
| tgcagtatta gtcattttc atacttgtgg tccacccaca cttgtaacac ttgtaacagt | 7620 |
| gcttttaggc acatattttt tgcatttcta aagggcttta attgcacacc ttggctttac | 7680 |
| atattatgtg tgtttgccaa caccacccta cacatcctgc caactttaag ttaaaacatg | 7740 |
| catgtaaaac attactcact gtattacaca ttgttatatg cacacaggtg tgtccaaccg | 7800 |
| atttggatta cagttttata agcatttctt tttattatag ttagtaacaa t | 7851 |

<210> SEQ ID NO 16
<211> LENGTH: 2602
<212> TYPE: DNA
<213> ORGANISM: Homo sapiens

<400> SEQUENCE: 16

| | |
|---|---|
| gagccgcggc taaggaacgc gggccgccca cccgctcccg gtgcagcggc ctccgcgccg | 60 |
| ggttttggcg cctcccgcgg gcgcccccct cctcacggcg agcgctgcca cgtcagacga | 120 |
| agggcgcagc gagcgtcctg atccttccgc ccggacgctc aggacagcgg cccgctgctc | 180 |
| ataagactcg gccttagaac cccagtatca gcagaaggac attttaggac gggacttggg | 240 |
| tgactctagg gcactggttt tctttccaga gagcggaaca ggcgaggaaa agtagtccct | 300 |

|  |  |
|---|---|
| tctcggcgat tctgcggagg gatctccgtg gggcggtgaa cgccgatgat tatataagga | 360 |
| cgcgccgggt gtggcacagc tagttccgtc gcagccggga tttgggtcgc agttcttgtt | 420 |
| tgtggatcgc tgtgatcgtc acttgacaat gcagatcttc gtgaagactc tgactggtaa | 480 |
| gaccatcacc ctcgaggttg agcccagtga caccatcgag aatgtcaagg caaagatcca | 540 |
| agataaggaa ggcatccctc ctgaccagca gaggctgatc tttgctggaa acagctgga | 600 |
| agatgggcgc accctgtctg actacaacat ccagaaagag tccaccctgc acctggtgct | 660 |
| ccgtctcaga ggtgggatgc aaatcttcgt gaagacactc actggcaaga ccatcaccct | 720 |
| tgaggtcgag cccagtgaca ccatcgagaa cgtcaaagca agatccagg acaaggaagg | 780 |
| cattcctcct gaccagcaga ggttgatctt tgccggaaag cagctggaag atgggcgcac | 840 |
| cctgtctgac tacaacatcc agaaagagtc taccctgcac ctggtgctcc gtctcagagg | 900 |
| tgggatgcag atcttcgtga agaccctgac tggtaagacc atcaccctcg aggtggagcc | 960 |
| cagtgacacc atcgagaatg tcaaggcaaa gatccaagat aaggaaggca ttccttctga | 1020 |
| tcagcagagg ttgatctttg ccggaaaaca gctggaagat ggtcgtaccc tgtctgacta | 1080 |
| caacatccag aaagagtcca ccttgcacct ggtactccgt ctcagaggtg ggatgcaaat | 1140 |
| cttcgtgaag acactcactg gcaagaccat cacccttgag gtcgagccca gtgacactat | 1200 |
| cgagaacgtc aaagcaaaga tccaagacaa ggaaggcatt cctcctgacc agcagaggtt | 1260 |
| gatctttgcc ggaaagcagc tggaagatgg gcgcaccctg tctgactaca acatccagaa | 1320 |
| agagtctacc ctgcacctgg tgctccgtct cagaggtggg atgcagatct tcgtgaagac | 1380 |
| cctgactggt aagaccatca ctctcgaagt ggagccgagt gacaccattg agaatgtcaa | 1440 |
| ggcaaagatc caagacaagg aaggcatccc tcctgaccag cagaggttga tctttgccgg | 1500 |
| aaaacagctg gaagatggtc gtaccctgtc tgactacaac atccagaaag agtccacctt | 1560 |
| gcacctggtg ctccgtctca gaggtgggat gcagatcttc gtgaagaccc tgactggtaa | 1620 |
| gaccatcact ctcgaggtgg agccgagtga caccattgag aatgtcaagg caaagatcca | 1680 |
| agacaaggaa ggcatccctc ctgaccagca gaggttgatc tttgctggga acagctgga | 1740 |
| agatggacgc accctgtctg actacaacat ccagaaagag tccaccctgc acctggtgct | 1800 |
| ccgtcttaga ggtgggatgc agatcttcgt gaagaccctg actggtaaga ccatcactct | 1860 |
| cgaagtggag ccgagtgaca ccattgagaa tgtcaaggca aagatccaag acaaggaagg | 1920 |
| catccctcct gaccagcaga ggttgatctt tgctgggaaa cagctggaag atggacgcac | 1980 |
| cctgtctgac tacaacatcc agaaagagtc caccctgcac ctggtgctcc gtcttagagg | 2040 |
| tgggatgcag atcttcgtga agaccctgac tggtaagacc atcactctcg aagtggagcc | 2100 |
| gagtgacacc attgagaatg tcaaggcaaa gatccaagac aaggaaggca tccctcctga | 2160 |
| ccagcagagg ttgatctttg ctgggaaaca gctggaagat ggacgcaccc tgtctgacta | 2220 |
| caacatccag aaagagtcca ccctgcacct ggtgctccgt ctcagaggtg ggatgcaaat | 2280 |
| cttcgtgaag accctgactg gtaagaccat caccctcgag gtggagccca gtgacaccat | 2340 |
| cgagaatgtc aaggcaaaga tccaagataa ggaaggcatc cctcctgatc agcagaggtt | 2400 |
| gatctttgct gggaaacagc tggaagatgg acgcaccctg tctgactaca acatccagaa | 2460 |
| agagtccact ctgcacttgg tcctgcgctt gagggggggt gtctaagttt ccccttttaa | 2520 |
| ggtttcaaca aatttcattg cactttcctt tcaataaagt gttgcattc ccaaaaaaaa | 2580 |
| aaaaaaaaaa aaaaaaaaa aa | 2602 |

-continued

```
<210> SEQ ID NO 17
<211> LENGTH: 685
<212> TYPE: PRT
<213> ORGANISM: Homo sapiens

<400> SEQUENCE: 17
```

| Met | Gln | Ile | Phe | Val | Lys | Thr | Leu | Thr | Gly | Lys | Thr | Ile | Thr | Leu | Glu |
|---|---|---|---|---|---|---|---|---|---|---|---|---|---|---|---|
| 1 | | | | 5 | | | | | 10 | | | | | 15 | |

| Val | Glu | Pro | Ser | Asp | Thr | Ile | Glu | Asn | Val | Lys | Ala | Lys | Ile | Gln | Asp |
|---|---|---|---|---|---|---|---|---|---|---|---|---|---|---|---|
| | | | 20 | | | | | 25 | | | | | 30 | | |

| Lys | Glu | Gly | Ile | Pro | Pro | Asp | Gln | Gln | Arg | Leu | Ile | Phe | Ala | Gly | Lys |
|---|---|---|---|---|---|---|---|---|---|---|---|---|---|---|---|
| | | | 35 | | | | | 40 | | | | | 45 | | |

| Gln | Leu | Glu | Asp | Gly | Arg | Thr | Leu | Ser | Asp | Tyr | Asn | Ile | Gln | Lys | Glu |
|---|---|---|---|---|---|---|---|---|---|---|---|---|---|---|---|
| | 50 | | | | | 55 | | | | | 60 | | | | |

| Ser | Thr | Leu | His | Leu | Val | Leu | Arg | Leu | Arg | Gly | Gly | Met | Gln | Ile | Phe |
|---|---|---|---|---|---|---|---|---|---|---|---|---|---|---|---|
| 65 | | | | 70 | | | | | 75 | | | | | 80 | |

| Val | Lys | Thr | Leu | Thr | Gly | Lys | Thr | Ile | Thr | Leu | Glu | Val | Glu | Pro | Ser |
|---|---|---|---|---|---|---|---|---|---|---|---|---|---|---|---|
| | | | | 85 | | | | | 90 | | | | | 95 | |

| Asp | Thr | Ile | Glu | Asn | Val | Lys | Ala | Lys | Ile | Gln | Asp | Lys | Glu | Gly | Ile |
|---|---|---|---|---|---|---|---|---|---|---|---|---|---|---|---|
| | | | 100 | | | | | 105 | | | | | 110 | | |

| Pro | Pro | Asp | Gln | Gln | Arg | Leu | Ile | Phe | Ala | Gly | Lys | Gln | Leu | Glu | Asp |
|---|---|---|---|---|---|---|---|---|---|---|---|---|---|---|---|
| | | | 115 | | | | | 120 | | | | | 125 | | |

| Gly | Arg | Thr | Leu | Ser | Asp | Tyr | Asn | Ile | Gln | Lys | Glu | Ser | Thr | Leu | His |
|---|---|---|---|---|---|---|---|---|---|---|---|---|---|---|---|
| | 130 | | | | | 135 | | | | | 140 | | | | |

| Leu | Val | Leu | Arg | Leu | Arg | Gly | Gly | Met | Gln | Ile | Phe | Val | Lys | Thr | Leu |
|---|---|---|---|---|---|---|---|---|---|---|---|---|---|---|---|
| 145 | | | | 150 | | | | | 155 | | | | | 160 | |

| Thr | Gly | Lys | Thr | Ile | Thr | Leu | Glu | Val | Glu | Pro | Ser | Asp | Thr | Ile | Glu |
|---|---|---|---|---|---|---|---|---|---|---|---|---|---|---|---|
| | | | | 165 | | | | | 170 | | | | | 175 | |

| Asn | Val | Lys | Ala | Lys | Ile | Gln | Asp | Lys | Glu | Gly | Ile | Pro | Ser | Asp | Gln |
|---|---|---|---|---|---|---|---|---|---|---|---|---|---|---|---|
| | | | 180 | | | | | 185 | | | | | 190 | | |

| Gln | Arg | Leu | Ile | Phe | Ala | Gly | Lys | Gln | Leu | Glu | Asp | Gly | Arg | Thr | Leu |
|---|---|---|---|---|---|---|---|---|---|---|---|---|---|---|---|
| | | | 195 | | | | | 200 | | | | | 205 | | |

| Ser | Asp | Tyr | Asn | Ile | Gln | Lys | Glu | Ser | Thr | Leu | His | Leu | Val | Leu | Arg |
|---|---|---|---|---|---|---|---|---|---|---|---|---|---|---|---|
| | 210 | | | | | 215 | | | | | 220 | | | | |

| Leu | Arg | Gly | Gly | Met | Gln | Ile | Phe | Val | Lys | Thr | Leu | Thr | Gly | Lys | Thr |
|---|---|---|---|---|---|---|---|---|---|---|---|---|---|---|---|
| 225 | | | | 230 | | | | | 235 | | | | | 240 | |

| Ile | Thr | Leu | Glu | Val | Glu | Pro | Ser | Asp | Thr | Ile | Glu | Asn | Val | Lys | Ala |
|---|---|---|---|---|---|---|---|---|---|---|---|---|---|---|---|
| | | | | 245 | | | | | 250 | | | | | 255 | |

| Lys | Ile | Gln | Asp | Lys | Glu | Gly | Ile | Pro | Pro | Asp | Gln | Gln | Arg | Leu | Ile |
|---|---|---|---|---|---|---|---|---|---|---|---|---|---|---|---|
| | | | 260 | | | | | 265 | | | | | 270 | | |

| Phe | Ala | Gly | Lys | Gln | Leu | Glu | Asp | Gly | Arg | Thr | Leu | Ser | Asp | Tyr | Asn |
|---|---|---|---|---|---|---|---|---|---|---|---|---|---|---|---|
| | | | 275 | | | | | 280 | | | | | 285 | | |

| Ile | Gln | Lys | Glu | Ser | Thr | Leu | His | Leu | Val | Leu | Arg | Leu | Arg | Gly | Gly |
|---|---|---|---|---|---|---|---|---|---|---|---|---|---|---|---|
| | 290 | | | | | 295 | | | | | 300 | | | | |

| Met | Gln | Ile | Phe | Val | Lys | Thr | Leu | Thr | Gly | Lys | Thr | Ile | Thr | Leu | Glu |
|---|---|---|---|---|---|---|---|---|---|---|---|---|---|---|---|
| 305 | | | | 310 | | | | | 315 | | | | | 320 | |

| Val | Glu | Pro | Ser | Asp | Thr | Ile | Glu | Asn | Val | Lys | Ala | Lys | Ile | Gln | Asp |
|---|---|---|---|---|---|---|---|---|---|---|---|---|---|---|---|
| | | | | 325 | | | | | 330 | | | | | 335 | |

| Lys | Glu | Gly | Ile | Pro | Pro | Asp | Gln | Gln | Arg | Leu | Ile | Phe | Ala | Gly | Lys |
|---|---|---|---|---|---|---|---|---|---|---|---|---|---|---|---|
| | | | 340 | | | | | 345 | | | | | 350 | | |

| Gln | Leu | Glu | Asp | Gly | Arg | Thr | Leu | Ser | Asp | Tyr | Asn | Ile | Gln | Lys | Glu |
|---|---|---|---|---|---|---|---|---|---|---|---|---|---|---|---|
| | | | 355 | | | | | 360 | | | | | 365 | | |

| Ser | Thr | Leu | His | Leu | Val | Leu | Arg | Leu | Arg | Gly | Gly | Met | Gln | Ile | Phe |
|---|---|---|---|---|---|---|---|---|---|---|---|---|---|---|---|
| | 370 | | | | | 375 | | | | | 380 | | | | |

```
Val Lys Thr Leu Thr Gly Lys Thr Ile Thr Leu Glu Val Glu Pro Ser
385                 390                 395                 400

Asp Thr Ile Glu Asn Val Lys Ala Lys Ile Gln Asp Lys Glu Gly Ile
            405                 410                 415

Pro Pro Asp Gln Gln Arg Leu Ile Phe Ala Gly Lys Gln Leu Glu Asp
            420                 425                 430

Gly Arg Thr Leu Ser Asp Tyr Asn Ile Gln Lys Glu Ser Thr Leu His
        435                 440                 445

Leu Val Leu Arg Leu Arg Gly Met Gln Ile Phe Val Lys Thr Leu
    450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
            485                 490                 495

Gln Arg Leu Ile Phe Ala Gly Lys Gln Leu Glu Asp Gly Arg Thr Leu
            500                 505                 510

Ser Asp Tyr Asn Ile Gln Lys Glu Ser Thr Leu His Leu Val Leu Arg
        515                 520                 525

Leu Arg Gly Gly Met Gln Ile Phe Val Lys Thr Leu Thr Gly Lys Thr
    530                 535                 540

Ile Thr Leu Glu Val Glu Pro Ser Asp Thr Ile Glu Asn Val Lys Ala
545                 550                 555                 560

Lys Ile Gln Asp Lys Glu Gly Ile Pro Pro Asp Gln Gln Arg Leu Ile
            565                 570                 575

Phe Ala Gly Lys Gln Leu Glu Asp Gly Arg Thr Leu Ser Asp Tyr Asn
            580                 585                 590

Ile Gln Lys Glu Ser Thr Leu His Leu Val Leu Arg Leu Arg Gly Gly
        595                 600                 605

Met Gln Ile Phe Val Lys Thr Leu Thr Gly Lys Thr Ile Thr Leu Glu
    610                 615                 620

Val Glu Pro Ser Asp Thr Ile Glu Asn Val Lys Ala Lys Ile Gln Asp
625                 630                 635                 640

Lys Glu Gly Ile Pro Pro Asp Gln Gln Arg Leu Ile Phe Ala Gly Lys
            645                 650                 655

Gln Leu Glu Asp Gly Arg Thr Leu Ser Asp Tyr Asn Ile Gln Lys Glu
            660                 665                 670

Ser Thr Leu His Leu Val Leu Arg Leu Arg Gly Gly Val
        675                 680                 685

<210> SEQ ID NO 18
<211> LENGTH: 1626
<212> TYPE: DNA
<213> ORGANISM: Homo sapiens

<400> SEQUENCE: 18
ctttgtggtt tggtctcagg gaagtagcag gcgccggttg agagaactac ggccctgtcg    60
gaaggtaacc tccggtgcaa acgaccatcg gcggcaggcg agcggtacgc ttggcgtccg   120
ggccttcctg ggcccgtctg aggaaacttg ctgctcgagg ccaggctgcc taggacctgt   180
cccttttttc tatactggct cccacatccg gttttttcct ccgggacggc ccttcggatg   240
cttgggccaa tgggaatcgc catttagggt gctccgccca ccgggtcgcg tagagcatcc   300
tggaagtcgt agtaaatctc tcgagagttc tctccgcacg cgggctggag aagcgggtcc   360
tacgcacgct tgttgtcgc gctttgcctc cgtccttccc cctactcccg ccttacctga    420
```

```
cttcctttc    ggaggaagat    ccttgagcag    ccgacgttgg    gacaaaggat    ttggagaaac      480
ccagggctaa    agtcacgttt    ttcctccttt    aagacttacc    tcaacacttc    actccatggc      540
agttcccgag    acccgcccta    accacactat    ttatatcaac    aacctcaatg    agaagatcaa      600
gaaggatgag    ctaaaaaagt    ccctgtacgc    catcttctcc    cagtttggcc    agatcctgga      660
tatcctggta    tcacggagcc    tgaagatgag    gggccaggcc    tttgtcatct    tcaaggaggt      720
cagcagcgcc    accaacgccc    tgcgctccat    gcagggtttc    cctttctatg    acaaacctat      780
gcgtatccag    tatgccaaga    ccgactcaga    tatcattgcc    aagatgaaag    gcaccttcgt      840
ggagcgggac    cgcaagcggg    agaagaggaa    gcccaagagc    caggagaccc    cggccaccaa      900
gaaggctgtg    caaggcgggg    agccaccccc    cgtggtgggg    gctgtccagg    ggcctgtccc      960
gggcatgccg    ccgatgactc    aggcgccccg    cattatgcac    acatgccgg     ccagccgcc      1020 ctacatgccg    cccctggta    tgatcccccc    gccaggcctt    gcacctggcc    agatcccacc      1080 agggccatg    ccccgcagc    agcttatgcc    aggacagatg    cccctgccc    agcctcttc       1140 tgagaatcca    ccgaatcaca    tcttgttcct    caccaacctg    ccagaggaga    ccaacgagct      1200
catgctgtcc    atgcttttca    atcagttccc    tggcttcaag    gaggtccgtc    tggtacccgg      1260
gcggcatgac    atcgccttcg    tggagtttga    caatgaggta    caggcagggg    cagctcgcga      1320
tgccctgcag    ggctttaaga    tcacgcagaa    caacgccatg    aagatctcct    tgccaagaa       1380 gtagcacctt    ttcccccat    gcctgcccct    tccctgttc    tgggggccacc   cctttccccc      1440 ttggctcagc    ccctgaagg    taagtccccc    cttgggggcc    ttcttggagc    cgtgtgtgag      1500
tgagtggtcg    ccacacagca    ttgtacccag    agtctgtccc    cagacattgc    acctggcgct      1560
gttaggccgg    aattaaagtg    gcttttgag    gtttggtttt    tcacaaaaaa    aaaaaaaaa       1620 aaaaaa                                                                                1626
```

<210> SEQ ID NO 19
<211> LENGTH: 282
<212> TYPE: PRT
<213> ORGANISM: Homo sapiens

<400> SEQUENCE: 19

```
Met Ala Val Pro Glu Thr Arg Pro Asn His Thr Ile Tyr Ile Asn Asn
1               5                   10                  15

Leu Asn Glu Lys Ile Lys Lys Asp Glu Leu Lys Lys Ser Leu Tyr Ala
            20                  25                  30

Ile Phe Ser Gln Phe Gly Gln Ile Leu Asp Ile Leu Val Ser Arg Ser
        35                  40                  45

Leu Lys Met Arg Gly Gln Ala Phe Val Ile Phe Lys Glu Val Ser Ser
    50                  55                  60

Ala Thr Asn Ala Leu Arg Ser Met Gln Gly Phe Pro Phe Tyr Asp Lys
65                  70                  75                  80

Pro Met Arg Ile Gln Tyr Ala Lys Thr Asp Ser Asp Ile Ile Ala Lys
                85                  90                  95

Met Lys Gly Thr Phe Val Glu Arg Asp Arg Lys Arg Glu Lys Arg Lys
            100                 105                 110

Pro Lys Ser Gln Glu Thr Pro Ala Thr Lys Lys Ala Val Gln Gly Gly
        115                 120                 125

Gly Ala Thr Pro Val Val Gly Ala Val Gln Gly Pro Val Pro Gly Met
    130                 135                 140

Pro Pro Met Thr Gln Ala Pro Arg Ile Met His His Met Pro Gly Gln
145                 150                 155                 160
```

```
Pro Pro Tyr Met Pro Pro Gly Met Ile Pro Pro Gly Leu Ala
            165                 170                 175

Pro Gly Gln Ile Pro Pro Gly Ala Met Pro Pro Gln Gln Leu Met Pro
        180                 185                 190

Gly Gln Met Pro Pro Ala Gln Pro Leu Ser Glu Asn Pro Pro Asn His
        195                 200                 205

Ile Leu Phe Leu Thr Asn Leu Pro Glu Glu Thr Asn Glu Leu Met Leu
    210                 215                 220

Ser Met Leu Phe Asn Gln Phe Pro Gly Phe Lys Glu Val Arg Leu Val
225                 230                 235                 240

Pro Gly Arg His Asp Ile Ala Phe Val Glu Phe Asp Asn Glu Val Gln
                245                 250                 255

Ala Gly Ala Ala Arg Asp Ala Leu Gln Gly Phe Lys Ile Thr Gln Asn
            260                 265                 270

Asn Ala Met Lys Ile Ser Phe Ala Lys Lys
            275                 280
```

<210> SEQ ID NO 20
<211> LENGTH: 3774
<212> TYPE: DNA
<213> ORGANISM: Homo sapiens

<400> SEQUENCE: 20

| | | | | | |
|---|---|---|---|---|---|
| ggctctggct | gagaacatgg | ccaatgacat | tgatgagctc | attggcattc | ccttccccaa | 60 |
| ccacagcagt | gaggtcctgt | gcagcctcaa | tgagcaacgg | cacgatggcc | tgctgtgtga | 120 |
| cgtgctcctg | gtggtgcagg | agcaggagta | tcggacccac | cgctccgtcc | tggctgcctg | 180 |
| cagcaagtac | ttcaagaagc | ttttcacagc | cggcacccta | gccagccagc | cctacgtcta | 240 |
| tgagatcgac | tttgtccagc | ctgaggctct | ggctgctatc | ctggagttcg | cctacacctc | 300 |
| cacgctcacc | atcaccgctg | gcaatgtcaa | gcacatcctc | aacgcagcca | ggatgctgga | 360 |
| gatccagtgc | atcgtgaacg | tgtgcctgga | gatcatggag | cctgggggg | acggggggga | 420 |
| ggaggatgac | aaggaggacg | atgacgacga | cgaagatgat | gatgatgagg | aggacgaaga | 480 |
| ggaggaggag | gaagaggagg | aggatgacga | tgatgacacg | gaggactttg | ctgaccaaga | 540 |
| aaacttgcct | gaccccagg | acatcagctg | ccaccaaagc | ccttccaaga | cagaccatct | 600 |
| cacagagaag | gcctattcag | acaccccag | ggacttccct | gactccttcc | aggctggcag | 660 |
| tcctggccat | ctgggggtga | tccgggactt | ctccatcgaa | tctctgctaa | gggagaacct | 720 |
| gtaccccaag | gccaacatcc | ccgacaggag | accctccttg | tctccattcg | ccccggactt | 780 |
| cttttccacac | ctctggccag | gggacttcgg | tgcctttgcc | cagctgcctg | agcagcccat | 840 |
| ggacagtggg | ccactggatc | tggtcatcaa | gaatcggaag | atcaaggagg | aggagaagga | 900 |
| ggagctgccc | ccaccccac | cgccaccctt | ccctaatgac | ttcttcaagg | acatgttccc | 960 |
| tgacctgccg | ggggggcctc | tgggacccat | caaggcggag | aacgactacg | gtgcctatct | 1020 |
| caacttcctg | agtgccaccc | acctgggagg | cctcttccca | ccctggcccc | tggtagaaga | 1080 |
| gcgcaagctg | aagcccaagg | cctctcagca | gtgccccatc | tgccacaaag | tcatcatggg | 1140 |
| ggccgggaag | ctgccgcggc | acatgaggac | ccataccggg | gagaagccat | acatgtgcac | 1200 |
| catctgcgag | gtccgcttca | ccaggcagga | caagctgaaa | atccacatgc | ggaagcacac | 1260 |
| aggggagcgg | ccctacctgt | gcatccactg | caacgccaag | ttcgtgcaca | actacgacct | 1320 |
| caagaaccac | atgcgcatcc | acacgggcgt | gcggccctac | cagtgcgagt | ctgctacaa | 1380 |
| gagcttcacg | cgctctgacc | acctgcaccg | ccacatcaag | cgccagagct | gccgcatggc | 1440 |

```
                                      -continued
acggccccga cgcggccgca agcctgctgc gtggagggcc gccagcctgc tcttcgggcc    1500
cggcggcccg gccccccgaca aggcggcctt cgtgatgccc cctgcgctgg gcgaggtggg   1560
cggccacctg ggcggcgcag ctgtgtgcct cccggcccc  agccccgcca agcacttcct    1620
ggcagcgccc aagggcgccc tgagcctgca agagctggag cggcagttcg aggagacaca    1680
gatgaagctg ttcgggcgcg cgcagctgga ggctgagagg aacgcggggg gcctcctggc    1740
cttcgcgctg gccgagaacg tggcggcggc gcggccctac ttcccgctgc ccgacccttg    1800
ggccgccggc ctggccggcc tccctgggct cgccggcctc aaccacgtgg cctccatgtc    1860
cgaagccaac aactaggctg gtccctgtcg gctccagccc accagccctc cagtccttct    1920
ccctccaggc ccactctacc ctaccccatg gatctgaact tttcatttta aaaacacaaa    1980
gggaaaatgg gaaataata  ataatactat cagtgatggc attttcccgg gctcctaaag    2040
cagctgcctc cttttgctgg tctgagacgg gcatctttc  ccaaaaggcc aggagcccgg    2100
gcctccctcc ctgtctctct ggctctcata tagaaacttg caccggccca tgccacaaag    2160
aactgggtgc ccaggggcac ttaggagctg ggtgagtcat gaggggtcag ggggtggttg    2220
gcctggtgcc cagccagcca cagcaggagg aggtaggggc tgggcatgca ccttggttaa    2280
gccccacccc ctatggcaaa gtctctgcca acactcctct gagggctcat tttccagtct    2340
ccagtggccc cggggtcttt ttgagaacta cccacctgcc acatagaaag aaatgctctg    2400
ttggcaggga ggcctcctgg aaccagtcag gaaccaggct ctggaaggcc cgggccattt    2460
cttccctgac ctgtcctgtg accttgacag gtcagccctc tgtagctcag tgtcacctgg    2520
ctatggaagg ggctggtaac tgaggtttcc gccctccacc tctaaacaca tacacaccta    2580 tcccccaga  gaatcacaga gatggtagaa gctttgtact ccccaagtcc atggggaaac    2640
agtttatctt tctggactta gttttatcac atccagctct atattagcat attagcatag    2700
gtgagaaata tggccagact agacagagat caggtcatca ggggagcttc cgagcttcag    2760
caaagcccac aggtagctct gcgaactcag aatgctaccc taccttccct gcaggccgct    2820
gttcatgtct ggactcctgg gggcgctatt taatgtttac cccatctcc  agtgccccct    2880 ccaaggctgt gcagtgtctt ggggctctca gggccaacat cgaagagatg ggggccacct    2940
cttaacacct ggcaacagtc tccctcatc  ctgattcctg acaacagaca aaacaccggt    3000
ttctagggtt tatctgtttg tttttttgagt tgagggttcc tcaggccctt ggcattgcta    3060
gtgatggtcc cctttgctgt gtgagaaccc cctcaaccc  ttcctcctcc ctctggggat    3120
gaagtgggag tatttggctc ccatttttg  acaaagggc  tcagtgcagg gaggtggagg    3180
cctctgaggt ttgaagggct ctgtgagtta gagttgtcac atgttctcct ggttcttgaa    3240
tttgcagcag gtcctgaaaa ggaaggctct gctggccccg tgccttcctg accttctctc    3300
tccttccctc ccctctcttt tcttgccaag tttgctttgg tttctgagca gcccagagag    3360
gaggagggtt cgtccccagg gagagcccag ggctggagtc cccaatccct gtgctatggg    3420
cacaaagaga cttcagctct tcctgttgcc ttggcttttt cctgagcaaa aacacaacaa    3480
acaaaaaggc cagagaagag cacagactct gtccctctca caactctcca gaagagaccc    3540
cctgattctt cacaccaccg gatgccactc cagccagcag gattgctaca cacaccctct    3600
gttctcagaa gtcatctgcc tgggcagccg cctctcagat tcctgtcttc gtttcagaca    3660
cttttctctg aagcatgccc atgtccacca gccaacgtgc cccgtgttc  cccccatca     3720 gccaagtgat tggggctgaa ccagacttta aagagagga  aaaaaaaaaa aaaa          3774
```

```
<210> SEQ ID NO 21
<211> LENGTH: 619
<212> TYPE: PRT
<213> ORGANISM: Homo sapiens

<400> SEQUENCE: 21

Met Ala Asn Asp Ile Asp Glu Leu Ile Gly Ile Pro Phe Pro Asn His
  1               5                  10                  15

Ser Ser Glu Val Leu Cys Ser Leu Asn Glu Gln Arg His Asp Gly Leu
             20                  25                  30

Leu Cys Asp Val Leu Leu Val Val Gln Glu Gln Glu Tyr Arg Thr His
         35                  40                  45

Arg Ser Val Leu Ala Ala Cys Ser Lys Tyr Phe Lys Lys Leu Phe Thr
 50                  55                  60

Ala Gly Thr Leu Ala Ser Gln Pro Tyr Val Tyr Glu Ile Asp Phe Val
 65                  70                  75                  80

Gln Pro Glu Ala Leu Ala Ala Ile Leu Glu Phe Ala Tyr Thr Ser Thr
                 85                  90                  95

Leu Thr Ile Thr Ala Gly Asn Val Lys His Ile Leu Asn Ala Ala Arg
            100                 105                 110

Met Leu Glu Ile Gln Cys Ile Val Asn Val Cys Leu Glu Ile Met Glu
        115                 120                 125

Pro Gly Gly Asp Gly Gly Glu Glu Asp Lys Glu Asp Asp Asp Asp
    130                 135                 140

Asp Glu Asp Asp Asp Asp Glu Glu Glu Glu Glu Glu Glu Glu
145                 150                 155                 160

Glu Glu Asp Asp Asp Asp Thr Glu Asp Phe Ala Asp Gln Glu Asn
                165                 170                 175

Leu Pro Asp Pro Gln Asp Ile Ser Cys His Gln Ser Pro Ser Lys Thr
            180                 185                 190

Asp His Leu Thr Glu Lys Ala Tyr Ser Asp Thr Pro Arg Asp Phe Pro
        195                 200                 205

Asp Ser Phe Gln Ala Gly Ser Pro Gly His Leu Gly Val Ile Arg Asp
    210                 215                 220

Phe Ser Ile Glu Ser Leu Leu Arg Glu Asn Leu Tyr Pro Lys Ala Asn
225                 230                 235                 240

Ile Pro Asp Arg Arg Pro Ser Leu Ser Pro Phe Ala Pro Asp Phe Phe
                245                 250                 255

Pro His Leu Trp Pro Gly Asp Phe Gly Ala Phe Ala Gln Leu Pro Glu
            260                 265                 270

Gln Pro Met Asp Ser Gly Pro Leu Asp Leu Val Ile Lys Asn Arg Lys
        275                 280                 285

Ile Lys Glu Glu Glu Lys Glu Leu Pro Pro Pro Pro Pro Pro
    290                 295                 300

Phe Pro Asn Asp Phe Phe Lys Asp Met Phe Pro Asp Leu Pro Gly Gly
305                 310                 315                 320

Pro Leu Gly Pro Ile Lys Ala Glu Asn Asp Tyr Gly Ala Tyr Leu Asn
                325                 330                 335

Phe Leu Ser Ala Thr His Leu Gly Gly Leu Phe Pro Trp Pro Leu
            340                 345                 350

Val Glu Glu Arg Lys Leu Lys Pro Lys Ala Ser Gln Gln Cys Pro Ile
        355                 360                 365

Cys His Lys Val Ile Met Gly Ala Gly Lys Leu Pro Arg His Met Arg
    370                 375                 380
```

```
Thr His Thr Gly Glu Lys Pro Tyr Met Cys Thr Ile Cys Glu Val Arg
385                 390                 395                 400

Phe Thr Arg Gln Asp Lys Leu Lys Ile His Met Arg Lys His Thr Gly
            405                 410                 415

Glu Arg Pro Tyr Leu Cys Ile His Cys Asn Ala Lys Phe Val His Asn
            420                 425                 430

Tyr Asp Leu Lys Asn His Met Arg Ile His Thr Gly Val Arg Pro Tyr
        435                 440                 445

Gln Cys Glu Phe Cys Tyr Lys Ser Phe Thr Arg Ser Asp His Leu His
    450                 455                 460

Arg His Ile Lys Arg Gln Ser Cys Arg Met Ala Arg Pro Arg Arg Gly
465                 470                 475                 480

Arg Lys Pro Ala Ala Trp Arg Ala Ala Ser Leu Leu Phe Gly Pro Gly
            485                 490                 495

Gly Pro Ala Pro Asp Lys Ala Ala Phe Val Met Pro Ala Leu Gly
        500                 505                 510

Glu Val Gly Gly His Leu Gly Gly Ala Ala Val Cys Leu Pro Gly Pro
            515                 520                 525

Ser Pro Ala Lys His Phe Leu Ala Ala Pro Lys Gly Ala Leu Ser Leu
        530                 535                 540

Gln Glu Leu Glu Arg Gln Phe Glu Glu Thr Gln Met Lys Leu Phe Gly
545                 550                 555                 560

Arg Ala Gln Leu Glu Ala Glu Arg Asn Ala Gly Gly Leu Leu Ala Phe
            565                 570                 575

Ala Leu Ala Glu Asn Val Ala Ala Ala Arg Pro Tyr Phe Pro Leu Pro
        580                 585                 590

Asp Pro Trp Ala Ala Gly Leu Ala Gly Leu Pro Gly Leu Ala Gly Leu
        595                 600                 605

Asn His Val Ala Ser Met Ser Glu Ala Asn Asn
        610                 615

<210> SEQ ID NO 22
<211> LENGTH: 10
<212> TYPE: PRT
<213> ORGANISM: HPV18

<400> SEQUENCE: 22

Met Ala Asp Pro Glu Gly His Gly Pro Asp
1               5                   10

<210> SEQ ID NO 23
<211> LENGTH: 10
<212> TYPE: PRT
<213> ORGANISM: HPV33

<400> SEQUENCE: 23

Met Ala Asp Pro Glu Gly Arg Gly Ala Asn
1               5                   10

<210> SEQ ID NO 24
<211> LENGTH: 10
<212> TYPE: PRT
<213> ORGANISM: HPV35

<400> SEQUENCE: 24

Met Ala Asp Pro Ala Gly Arg Gly Ala Asp
1               5                   10
```

<210> SEQ ID NO 25
<211> LENGTH: 21
<212> TYPE: DNA
<213> ORGANISM: Human papillomavirus type 52

<400> SEQUENCE: 25
ggaccctgaa ggacgtggtg c                                              21

<210> SEQ ID NO 26
<211> LENGTH: 24
<212> TYPE: DNA
<213> ORGANISM: Human papillomavirus type 58

<400> SEQUENCE: 26
tgaccctgaa ggacgtggtg caaa                                           24

<210> SEQ ID NO 27
<211> LENGTH: 11
<212> TYPE: DNA
<213> ORGANISM: Human papillomavirus type 52

<400> SEQUENCE: 27
ggaccctgaa g                                                         11

<210> SEQ ID NO 28
<211> LENGTH: 11
<212> TYPE: DNA
<213> ORGANISM: Human papillomavirus type 58

<400> SEQUENCE: 28
tgaccctgaa g                                                         11

<210> SEQ ID NO 29
<211> LENGTH: 10
<212> TYPE: DNA
<213> ORGANISM: Human papillomavirus type 52

<400> SEQUENCE: 29
gacgtggtgc                                                           10

<210> SEQ ID NO 30
<211> LENGTH: 13
<212> TYPE: DNA
<213> ORGANISM: Human papillomavirus type 58

<400> SEQUENCE: 30
gacgtggtgc aaa                                                       13

<210> SEQ ID NO 31
<211> LENGTH: 11
<212> TYPE: DNA
<213> ORGANISM: Human papillomavirus type 58

<400> SEQUENCE: 31
ctgaaggacg t                                                         11

<210> SEQ ID NO 32
<211> LENGTH: 7942
<212> TYPE: DNA
<213> ORGANISM: Human papillomavirus type 52

<400> SEQUENCE: 32

```
taaattataa tcttatacta gtaaaaaata gggtgtaacc gaaaacggtc agaccgaaac      60
cggtgtatat atatagaaca cagtgtagct aacgcacggc catgtttgag gatccagcaa     120
cacgaccccg gaccctgcac gaattgtgtg aggtgctgga agaatcggtg catgaaataa     180
ggctgcagtg tgtgcagtgc aaaaaagagc tacaacgaag agaggtatac aagtttctat     240
ttacagattt acgaatagta tatagagaca ataatccata tggcgtgtgt attatgtgcc     300
tacgcttttt atctaagata agtgaatata ggcattatca atattcactg tatgggaaaa     360
cattagaaga gagggtaaaa aaaccattaa gtgaaataac tattagatgt ataatttgtc     420
aaacgccatt atgtcctgaa gaaaagaaa gacatgttaa tgcaaacaag cgatttcata     480
atattatggg tcgttggaca gggcgctgtt cagagtgttg gagacccga cctgtgaccc     540
aagtgtaacg tcatgcgtgg agacaaagca actataaaag attatatatt agatctgcaa     600
cctgaaacaa ctgacctaca ctgctatgag caattaggtg acagctcaga tgaggaggat     660
acagatggtg tggaccggcc agatggacaa gcagaacaag ccacaagcaa ttactacatt     720
gtgacatatt gtcacagttg tgatagcaca ctacggctat gcattcatag cactgcgacg     780
gaccttcgta ctctacagca aatgctgttg ggcacattac aagttgtgtg ccccggctgt     840
gcacggctat aaacaaccct gcaatggagg accctgaagg tacagagggc gaaagggagg     900
gatgtacagg ctggtttgaa gtagaggcaa taatagaaaa acaaacagga gataacattt     960
cagaggacga ggatgaaaat gcatatgata gtggaacaga tctaatagat tttatagatg    1020
attcaaatat aaataatgaa caggcagaac atgaggcagc ccgggcattg tttaatgcac    1080
aggaagggga ggatgattta catgctgtgt ctgcagtaaa acgaaagttt acaagcagtc    1140
cggaaagtgc tgggcaagat ggtgtagaaa aacatggtag tccgcgtgca aaacacattt    1200
gtgtaaatac agagtgtgtt ttaccaaaac gcaaaccatg tcacgtagaa gacagcggct    1260
atggcaatag tgaagtggaa gcgcagcaga tggcagacca ggtagacggg caaaatggcg    1320
actggcaaag taacagtagt caatcaagtg gggtgggggc tagtaattca gatgtaagtt    1380
gtactagtat agaggacaat gaggaaaata gtaaatgaac gctaaaaagc atacaaaata    1440
ttatgtgcga aaatagcata aaaacaactg tattatttaa atttaaagaa acatatggtg    1500
ttagctttat ggaattagta agaccattta aaagtaatag aagtagttgt acagattggt    1560
gtattatagg aatgggagta acaccatcag ttgcagaagg attaaaagta ttaatacagc    1620
cctatagcat atatgcccat ttgcaatgtt taacatgtga cagaggcgtg cttatactgc    1680
tgctaattag gtttaaatgt ggaaaaaaca gattaacagt gtccaaacta atgtcacagc    1740
tgttaaaatat accagaaaca catatggtaa tagaaccacc aaaattacga agtgctacct    1800
gtgcattata ttggtataga acaggtttgt ctaatattag tgaggtatat ggtaccaccc    1860
cagaatggat agaacaacaa acagtattac agcatagctt tgacaatagc atattcgatt    1920
ttggagaaat ggtgcaatgg gcatatgatc atgatataac agatgatagt gacatagcat    1980
ataaatatgc acagttagca gatgtaaata gcaatgctgc agcattccta aaaagcaatt    2040
cgcaagcaaa aatagtaaag gactgtgcaa ccatgtgtag acattataaa cgggcagaaa    2100
gaaaacatat gaatattgga caatggatac agtatagatg tgatagaata gatgatggtg    2160
gagattggag gcctatagta agatttttaa gatatcaaga catagaattt acagccttt     2220
tagacgcatt taaaaaattt ttaaaaggta tacctaaaaa aaattgttta gtattatatg    2280
gacctgcaaa cacaggaaaa tcatatttg gaatgagttt aattaggttc ttaagtggat    2340
```

```
gtgtaatatc ctatgtaaac tcaaaaagcc attttttggct acaaccatta acagatgcaa    2400
aagtgggtat gatagatgat gtaacaccta tatgttggac atatatagat gattatatga    2460
gaaatgcact ggatggaaat gatatatcag tagatgtaaa gcatagagcc ttagtacaaa    2520
taaaatgccc accattaatt ttaacaacaa atacaaatgc aggaacagat cctaggtggc    2580
catatttaca tagtagattg gttgtgtttc atttcaaaaa cccatttcca tttgatgaaa    2640
atggcaatcc tatatatgaa attaacaacg aaaattggaa atcctttttc tcaaggacgt    2700
ggtgcaaatt agatttaata caggaagagg acaaggaaaa cgatggagtc gataccggca    2760
cgtttaaatg cagtgcagga aaaaatacta gatctatacg aagctgatag taatgaccta    2820
aacgcacaaa ttgaacattg gaaattgact cgaatggaat gtgttttgtt ttacaaagca    2880
aaggaactgg gaataactca tataggccac caggtggtgc caccaatggc agtgtctaag    2940
gcaaaggcct gccaagctat tgaactacaa ttggcattgg aggcattaaa caaaacacaa    3000
tatagcacag atggatggac attacaacaa acaagtctag aaatgtggcg tgcagaacca    3060
caaaaatact ttaaaaaaca tgggtataca ataacagtgc aatacgataa tgataaaaac    3120
aatactatgg attatacaaa ctggaaggaa atttatttac ttggtgagtg tgaatgtaca    3180
attgtagaag gacaagtaga ttactatggg ttatattatt ggtgtgatgg agaaaaaata    3240
tattttgtaa aatttagtaa cgatgcaaag caatattgtg taacaggagt atgggaagta    3300
catgtgggtg gtcaggtaat tgtttgtcct gcatctgtat ctagtaacga agtatccact    3360
actgaaactg ctgtccacct atgcaccgaa acctccaaga cctccgcagt gtccgtgggt    3420
gccaaagaca cacacctaca accaccacag aaacgacgac gaccagacgt cacagactcc    3480
agaaacacca gtaccccaa caaccttttg cggggacaac aatccgtgga cagtactaca    3540
cggggactcg tcactgcaac tgagtgcaca acaaaggac gggttgcaca tacaacttgt    3600
actgcaccta atacacct aaaaggtgat cctaatagtt taaaatgttt aagatatagg    3660
gtaaaaacac ataaaagttt gtatgttcaa atttcatcta cctggcattg gaccagtaat    3720
gaatgtacaa ataataaact aggtattgta acaataacgt acagtgatga aacacaacgt    3780
caacaatttt taaaaactgt taaaatacca aatactgtgc aagttataca aggtgtcatg    3840
tcattgtgat atttgtacat atgtatatat gtatgtgt atggtaaaca cccaacacaa    3900
gccaatattg ctgctattgt gtatatataa caatgttagg attatttgta ttttgttttta    3960 ttttgcttat ggtgttttgt gcagtgctta ggccgctctt gctatctata tcggtgtatg    4020
cgcaggtgtt ggtgctggtg cttttgctat gggtatctat tgggtcacca tttaaagtgt    4080 ttttttgta cctactgttt ttatattttc caatgttttg tattcactgt catgcacagt    4140
atttggcaca actgcaataa ctgtacatgt agattggcta catgcatata tgcaaaatat    4200 acttttcac ttttgtagtt tgtctaataa atactttat attttttaat agcttgtcgc    4260
aatgagatac agacggtcta cacggcacaa acgtgcttct gcaacacagc tatatcaaac    4320
atgcaaagcc tctggcacct gcccccccga tgttattcct aaagtggaag gcacaactat    4380
tgcagatcaa cttttaaaat atggcagcct aggggtgttt tttggaggtt tgggtatagg    4440
tacaggtgca ggctctggtg gtagggcagg ctatgtgcca ttgtccactc gtcctcccac    4500
tagtagtatt accacgtcca ccattcgtcc ccctgtaact gtagaaccca ttggtccctt    4560
agaaccatct atagtttcta tgatagaaga aacaacattt attgagtctg gcgcacctgc    4620
tccatctatt ccatcagcaa cagggtttga tgttacaaca tctgcaaata atactcctgc    4680
aataattaat gtaacatcta taggtgaatc atctgtacaa tcagtttcta cacatttaaa    4740
```

```
tcctacattc actgaaccat ctataataca gcccccggca cctgcagaag catctggtca    4800
tgtattgttt tctagtccaa ctattagtac acacacctat gaagaaatcc ctatggatac    4860
atttgttacc tctactgaca gcagcagtgt aacaagtagt acacctattc cagggtctcg    4920
ccctacgaca cgccttggtt tatatagccg tgccacacaa caggttaagg tagtcgaccc    4980
tgcttttatg tcatcaccac agaaattagt aacatataac aatcctgttt ttgagggcgt    5040
tgatacagat gaaactataa ttttttgatcg ttcacaactt ttacctgcac cggatcctga    5100
tttttttagac attatagctt tgcataggcc tgcattaacc tctcgaagag gtactgttag    5160
gtttagcagg cttggtaata aggccaccct acgtacacgt agtggaaaac aaattggggc    5220
acgggtacat tattatcatg atattagtcc tatccagcct gctgaagttc aggaagacat    5280
agaattgcaa cctttattac cacagtctgt gtccccttac actattaatg atggtttgta    5340
tgatgtgtat gcagattctt tgcagcaacc cacgtttcac ttaccttcca cactttctac    5400
ccataataat actttcactg tacctattaa tagtggtatt gactttgtat atcaacccac    5460
tatgtccatt gagtcaggtc ctgacattcc attaccttcg ttacccacac atactccttt    5520
tgttcctata gcccctacag ctccatctac atctattatt gttgatggta cagattttat    5580
tttacatcct agttattttt tactacgtcg caggcgtaaa cgttttccat attttttttac    5640
agatgtccgt gtggcggcct agtgaggcca ctgtgtacct gcctcctgta cctgtctcta    5700
aggttgtaag cactgatgag tatgtgtctc gcacaagcat ctattattat gcaggcagtt    5760
ctcgattact aacagtagga catccctatt tttctattaa aaacaccagt agtggtaatg    5820
gtaaaaaagt tttagttccc aaggtgtctg gcctgcaata cagggtattt agaattaaat    5880
tgccggaccc taataaattt ggttttccag atacatcttt ttataaccca gaaacccaaa    5940
ggttggtgtg ggcctgtaca ggcttggaaa ttggtagggg acagccttta ggtgtgggta    6000
ttagtgggca tcctttatta aacaagtttg atgatactga aaccagtaac aaatatgctg    6060
gtaaacctgg tatagataat agggaatgtt tatctatgga ttataagcag actcagttat    6120
gcattttagg atgcaaacct cctataggtg aacattgggg taagggaacc ccttgtaata    6180
ataattcagg aaatcctggg gattgtcctc ccctacagct cattaacagt gtaatacagg    6240
atgggacat ggtagataca ggatttggtt gcatggattt taatacccttg caagctagta    6300
aaagtgatgt gcccattgat atatgtagca gtgtatgtaa gtatccagat tatttgcaaa    6360
tggctagcga gccatatggt gacagtttgt ctttttttct tagacgtgag caaatgtttg    6420
ttagacactt ttttaatagg gccggtacct taggtgaccc tgtgccaggt gatttatata    6480
tacaagggtc taactctggc aatactgcca ctgtacaaag cagtgctttt ttcctactc    6540
ctagtggttc tatggtaacc tcagaatccc aattatttaa taaaccgtac tggttacaac    6600
gtgcgcaggg ccacaataat ggcatatgtt ggggcaatca gttgtttgtc acagttgtgg    6660
ataccactcg tagcactaac atgactttat gtgctgaggt taaaaaggaa agcacatata    6720
aaaatgaaaa ttttaaggaa taccttcgtc atggcgagga atttgattta caatttattt    6780
ttcaattgtg caaaattaca ttaacagctg atgttatgac atacattcat aagatggatg    6840
ccactatttt agaggactgg caatttggcc ttaccccacc accgtctgca tctttggagg    6900
acacatacag atttgtcact tctactgcta taacttgtca aaaaacaca ccacctaaag    6960
gaaaggaaga tccttttaaag gactatatgt tttgggaggt ggatttaaaa gaaaagtttt    7020
ctgcagattt agatcagttt cctttaggta ggaagttttt gttacaggca gggctacagg    7080
ctaggcccaa actaaaacgc cctgcatcat cggcccacg tacctccaca aagaagaaaa    7140
```

| | |
|---|---|
| aggttaaaag gtaaccattg tctgttgggt aattgtctgt gtcatgtatg tgttgtgtat | 7200 |
| gtcaaacaca ggttaaaagg taaccattgt ttgttatgta attgttttgt gtgtgtactg | 7260 |
| tgttgtttgc atgttatgta tgtgtgtgca tgtttgttgt atttgtcagt tcctgtatgt | 7320 |
| atgttttgtg tatgtattaa taaagtactg tatttactaa actatttata gtagtcttat | 7380 |
| gttatgttat ggttgcaccc acatgagtaa caatacagtt gctcctaatc tattgcatct | 7440 |
| cctgccctac cctgtgtccc ctgccctacc ctgtgtccta ctttgttaca ctactaatta | 7500 |
| gccttatact ctccattttg taccattttg tactatccac catttaaat cctaaccgaa | 7560 |
| ttcggttggt cttggcacaa ctttggttgt ccttggcaca gtaacaacta ttttttatata | 7620 |
| agtttcagca aactgcttaa tccttttggtt tcctgcagtc cactggtcta cacttgttgt | 7680 |
| cccgcctaaa ctgacttctt gctgactcac aggtcctgca gtgcagctaa acaatacatt | 7740 |
| gcctaacatt gcatgtttta aactgctttt aggcacatat tttatttaaa ctttcaatgc | 7800 |
| actaattaca gtgttggctt acacaagtac atcctacgcc aaatatgtct tgtaaaacat | 7860 |
| gattaaatac tgttactcac caggtgtgca ctacacgacc ggttacggtt accgtaccca | 7920 |
| caaccacttt tttttataat ta | 7942 |

<210> SEQ ID NO 33
<211> LENGTH: 7824
<212> TYPE: DNA
<213> ORGANISM: Human papillomavirus type 58

<400> SEQUENCE: 33

| | |
|---|---|
| ctaaactata atgccaaatc ttgtaaaaac tagggtgtaa ccgaaaacgg tctgaccgaa | 60 |
| accggtgcat atataaagca gacattttt ggtaggctac tgcaggacta tgttccagga | 120 |
| cgcagaggag aaaccacgga cattgcatga tttgtgtcag gcgttggaga catctgtgca | 180 |
| tgaaatcgaa ttgaaatgcg ttgaatgcaa aaagactttg cagcgatctg aggtatatga | 240 |
| cttgtatttt gcagatttaa gaatagtgta tagagatgga atccatttg cagtatgtaa | 300 |
| agtgtgctta cgattgctat ctaaaataag tgagtataga cattataatt attcgctata | 360 |
| tggagacaca ttagaacaaa cactaaaaaa gtgtttaaat gaaatattaa ttagatgtat | 420 |
| tatttgtcaa agaccattgt gtccacaaga aaaaaaagg catgtggatt taaacaaaag | 480 |
| gtttcataat atttcgggtc gttggacagg gcgctgtgca gtgtgttgga gaccccgacg | 540 |
| tagacaaaca caagtgtaac ctgtaacaac gccatgagag gaaacaaccc aacgctaaga | 600 |
| gaatatattt tagatttaca tcctgaacca actgacctat tctgctatga gcaattatgt | 660 |
| gacagctcag acgaggatga aataggcttg gacgggccag atggacaagc acaaccggcc | 720 |
| acagctaatt actacattgt aacttgttgt tacacttgtg gcaccacggt tcgtttgtgt | 780 |
| atcaacagta caacaaccga cgtacgaacc ctacagcagc tgcttatggg cacatgtacc | 840 |
| attgtgtgcc ctagctgtgc acagcaataa acaccatctg caatggatga ccctgaaggt | 900 |
| acaaacgggg taggggcggg ctgtactggc tggtttgagg tagaagcggt aatagaacga | 960 |
| agaacaggag ataatatttc agatgatgag gacgaaacag cagacgatag tggtacagat | 1020 |
| ttaatagagt ttatagatga ttcagtacaa agtactacac aggcagaagc agaggcagcc | 1080 |
| cgagcgttgt ttaatgtaca ggaagggggtg gacgatataa atgctgtgtg tgcactaaaa | 1140 |
| cgaaagtttg cagcatgctc agaaagtgct gtagaggact gtgtggaccg ggctgcaaat | 1200 |
| gtgtgtgtat cgtggaaata taaaaataaa gaatgcacac acagaaaacg aaaaattatt | 1260 |
| gagctagaag acagcggata tggcaatact gaagtggaaa ctgagcagat ggcacaccag | 1320 |

```
gtagaaagcc aaaatggcga cgcagactta aatgactcgg agtctagtgg ggtgggggct    1380
agttcagatg taagcagtga aacggatgta gacagttgta atactgttcc attacaaaat    1440
attagtaata ttctacataa cagtaatact aaagcaacgc tattatataa attcaaagaa    1500
gcttatggag taagttttat ggaattagtt agaccattta aaagtgataa aacaagctgt    1560
acagattggt gtataacagg gtatggaata agtccctccg tagcagaaag tttaaaagta    1620
ctaattaaac agcacagtat atatacacac ctacaatgtt taacgtgtga cagaggaatt    1680
atattattat tgttaattag atttaaatgt agcaaaaata gattaactgt ggcaaaatta    1740
atgagtaatt tactatcaat tcctgaaaca tgtatgatta tcgagccacc aaaattacga    1800
agtcaagcat gtgccttata ttggtttaga acagcaatgt caaatataag tgatgtgcaa    1860
gggacaacac cagaatggat agatagatta acagtgttac agcatagctt taatgatgat    1920
atatttgatt taagtgaaat gatacaatgg gcatatgata atgacattac agatgatagt    1980
gacattgcat ataaatatgc acagttagca gatgttaata gtaatgcagc agcattttta    2040
agaagcaatg cacaagcaaa aatagtaaaa gactgtggcg ttatgtgcag acattataaa    2100
agagcagaaa agcgtggtat gacaatggga caatggatac aaagtaggtg tgaaaaaaca    2160
aatgatggag gtaattggag accaatagta caattttttaa gatatcaaaa tattgaattt    2220
acagcatttt tagttgcatt taaacagttt ttacaaggtg taccaaaaaa aagttgtatg    2280
ttactgtgtg gcccagcaaa tacagggaaa tcatattttg aatgagtttt aatacatttt    2340
ttaaaaggat gcattatttc atatgtaaat tccaaaagtc atttttggtt gcagccatta    2400
tcagatgcta aactaggtat gatagatgat gtaacagcca taagctggac atatatagat    2460
gattatatga gaaatgcatt agatggtaac gacatttcaa tagatgtaaa acatagggca    2520
ttagtacaat taaaatgtcc accattaata attacctcaa atacaaatgc aggcaaagat    2580
tcacgatggc catatttgca cagtagacta acagtatttg aatttaacaa tccatttcca    2640
tttgatgcaa atggtaatcc agtgtataaa ataaatgatg aaaattggaa atcctttttc    2700
tcaaggacgt ggtgcaaatt aggcttaata gaggaagagg acaaggaaaa cgatggagga    2760
aatatcagca cgtttaagtg cagtgcagga caaaatccta gacatatacg aagctgataa    2820
aaatgattta acatcacaaa ttgaacattg gaaactaata cgcatggagt gtgctataat    2880
gtatacagcc agacaaatgg gaatatcaca tttgtgccac caggtggtgc cgtcattggt    2940
agcatcaaag actaaagcgt tcaagtaat tgaactgcaa atggcattag agacattaaa    3000
tgcatcacca tataaaacag atgaatggac attgcaacaa caagcttag aagtgtggtt    3060
atcagagcca caaaaatgct ttaaaaaaaa aggcataaca gtaactgtac aatatgacaa    3120
tgataaagca aacacaatgg attatacaaa ttggagtgaa atatatatta ttgaggaaac    3180
aacatgtact ttggtagcag gagaagttga ctatgtgggg ttgtattata tacatggcaa    3240
tgaaagacg tattttaaat atttttaaga ggatgcaaaa aagtactcta aaacacaatt    3300
atgggaggta catgtgggta gtcgggtaat tgtatgtcct acatctatac ctagtgatca    3360
aatatccact actgaaactg ctgacccaaa gaccaccgag gccaccaaca acgaaagtac    3420
acagggggaca aagcgacgac gactcgattt accagactcc agagacaaca cccagtactc    3480
cacaaagtat acagactgcg ccgtggacag tagaccacga ggaggaggac tacacagtac    3540
aactaactgt acatacaaag ggcggaacgt gtgtagttct aaagtttcac ctatcgtgca    3600
tttaaaaggt gacccaaata gtttaaaatg tttaagatat agattaaaac catttaaaga    3660
cttatactgt aatatgtcat ccacatggca ttggaccagt gatgacaaag gtgacaaagt    3720
```

```
aggaattgtt actgtaacat acacaacgga aacacaacga caactgttttt taaacactgt    3780
taaaatacca cccactgtgc aaataagtac tggtgttatg tcattgtaat tgtattgtac    3840
aattactgta tgtaaaccac aagccaatat gtgctgctaa gtgtatatac aatgatatta    3900
cctattttg ttgtttgttt tatactgttt ttatgcttgt gcattttttt gcggccattg     3960
gtgctatcta tttctatata tgcttggttg ctggtgttgg tgttgctgct ttgggtgtct    4020
gtggggtcgg ctctacgaat tttttctgt tacttaatat ttttatatat accaatgatg     4080
tgtattaatt ttcatgcaca atacttaacc caacaagact aactgtatac tggttctgca    4140
catggtggta tggtattgta aatatttact gttgtgtgtg ttgttttat tattttata      4200
catttactaa taaatacttt tatatttta gcactgtctt attatgagac acaaacggtc     4260
tacaaggcgc aagcgtgcat ctgctacaca actttaccaa acatgcaagg cctcaggcac    4320
ctgcccacct gatgttatac ccaaagttga aggcactact atagcagatc aaatattacg    4380
atatggtagc ttaggggtgt tttttggagg tttaggcatt ggtacagggt cgggtacagg    4440
tggcaggact ggatatgtgc cccttggtag tacccaccg tctgaggcta tacctttaca     4500
gcccatacgt cccccagtta ccgttgatac tgtgggcct ttggattctt ctattgtatc     4560
tttaatagag gaatctagtt ttatagacgc cggtgcacca gccccatcaa ttcccactcc    4620
atctggtttt gatattacca cctctgcaga tactacacct gcaatactta atgtttcctc    4680
tattggagaa tcatctatac aaactgtttc tacacattta aatccctcct ttactgagcc    4740
atccgtactc cgccctcctg cacctgcaga ggcctctgga catttaatat tttcctctcc    4800
tactgttagc acacatagtt atgaaaacat accaatggat accttttgtta tttctactga    4860
cagtggcaat gtcacgtcta gcacacccat tccagggtct cgccctgtgg cacgccttgg    4920
tttatacagt cgcaacaccc aacaagttaa ggttgttgac cctgcttttt taacatctcc    4980
tcatagactt gtaacatatg ataatccagc atttgaaggc tttaaccctg aggacacatt    5040
gcagtttcaa catagtgaca tatcgcctgc tcctgatcct gattttctag atattgttgc    5100
attacacaga cctgcattaa cctctcgcag gggtactgta cgttatagta gggttgggca    5160
aaaggctaca cttcgtactc gcagtggaaa gcaaataggg gctaaagtac attactacca    5220
agacttaagt cccatacagc ctgtccagga acaggtacaa cagcagcaac aatttgaatt    5280
acaatcttta aatacttctg tttctcccta tagtattaat gatggacttt atgatattta    5340
tgctgacgat gctgatacta tacatgattt tcagagtcct ctgcactcac atacgtcctt    5400
tgccaccaca cgtaccagta atgtgtccat accattaaat actggatttg acactcctct    5460
tgtgtcattg gaacctggtc cagacattgc atcttctgta acatctatgt ctagtccatt    5520
tattcctata tctccactaa ctccttttaa taccataatt gtggatggtg ctgatttat     5580
gttgcaccct agctatttta ttttgcgtcg cagacgtaaa cgttttccat attttttgc     5640
agatgtccgt gtggcggcct agtgaggcca ctgtgtacct gcctcctgtg cctgtgtcta    5700
aggttgtaag cactgatgaa tatgtgtcac gcacaagcat ttattattat gctggcagtt    5760
ccagactttt ggctgttggc aatccatatt tttccatcaa aagtcccaat aacaataaaa    5820
aagtattagt tcccaaggta tcaggcttac agtatagggt ctttagggtg cgtttacctg    5880
atcccaataa atttggtttt cctgatacat cttttttataa ccctgataca caacgtttgg    5940
tctgggcatg tgtaggcctt gaaataggta ggggacagcc attgggtgtt ggcgtaagtg    6000
gtcatcctta tttaaataaa tttgatgaca ctgaaaccag taacagatat cccgcacagc    6060
cagggtctga taacagggaa tgcttatcta tggattataa acaaacacaa ttatgtttaa    6120
```

```
ttggctgtaa acctcccact ggtgagcatt ggggtaaagg tgttgcctgt aacaataatg    6180
cagctgctac tgattgtcct ccattggaac ttttaattc tattattgag gatggtgaca    6240
tggtagatac agggtttgga tgcatggact ttggtacatt gcaggctaat aaaagtgatg    6300
tgcctattga tatttgtaac agtacatgca aatatccaga ttatttaaaa atggccagtg    6360
aaccttatgg ggatagtttg ttcttttttc ttagacgtga gcagatgttt gttagacact    6420
tttttaatag ggctggaaaa cttggcgagg ctgtcccgga tgacctttat attaaagggt    6480
ccggtaatac tgcagttatc aaagtagtg cattttttcc aactcctagt ggctctatag    6540
ttacctcaga atcacaatta tttaataagc cttattggct acagcgtgca caaggtcata    6600
acaatggcat ttgctggggc aatcagttat ttgttaccgt ggttgatacc actcgtagca    6660
ctaatatgac attatgcact gaagtaacta aggaaggtac atataaaaat gataatttta    6720
aggaatatgt acgtcatgtt gaagaatatg acttacagtt tgtttttcag ctttgcaaaa    6780
ttacactaac tgcagagata atgacatata tacatactat ggattccaat attttggagg    6840
actggcaatt tggtttaaca cctcctccgt ctgccagttt acaggacaca tatagatttg    6900
ttacctccca ggctattact tgccaaaaaa cagcaccccc taaagaaaag gaagatccat    6960
taaataaata cttttttggg gaggttaact taaggaaaaa gttttctgca gatctagatc    7020
agtttccttt gggacgaaag tttttattac aatcaggcct taaagcaaag cccagactaa    7080
acgttcggc ccctactacc cgtgcaccat ccaccaaacg caaaaaggtt aaaaaataat    7140
tgttgtggta cttacactat tttattatac atgtttgttt gttttatgta tgtgttgtct    7200
gtttgtttat gtttgtgtat atgttgtatg tgttatgtgt catgtttgtg tacatgttct    7260
atgtccttgt cagtttcctg tttctgtata tatgtaataa actattgtgt gtattgtaaa    7320
ctatttgtat tgtttgggtg tatctatgag taaggtgctg tccctaaatt gccctacct    7380
gccctgccta ttatgcatac ctatgtaata gtatttgtat gatatgtatt ttatagtttt    7440
taacagtact gcctccattt tactttacct ccattttgtg catgtaaccg atttcggttg    7500
ctggcacaaa cgtgttttt ttaaactaca atttaaacaa tacagttaat cctttccctt    7560
cctgcactgc ttttgcctat acttgcatat gtgactcata tatacatgca gtgcagttgc    7620
aaaatgttta attatactca tagttttaaac atgcttatag gcacatattt taacttactt    7680
tcaatgctta agtgcagttt tggcttgcac aatagtttgt tatgccaaac tatgtcttgt    7740
aaaagtgact cactaacatt tattgccagg tgtggactaa ccgttttggg tcacattgtt    7800
catgtttcaa cattttatat aata                                            7824
```

<210> SEQ ID NO 34
<211> LENGTH: 10
<212> TYPE: PRT
<213> ORGANISM: Human papillomavirus type 52

<400> SEQUENCE: 34

Met Glu Asp Pro Glu Gly Arg Gly Ala Asn
1               5                   10

<210> SEQ ID NO 35
<211> LENGTH: 10
<212> TYPE: PRT
<213> ORGANISM: Human papillomavirus type 58

```
<400> SEQUENCE: 35

Met Asp Asp Pro Glu Gly Arg Gly Ala Asn
1               5                   10
```